(12) United States Patent
Watanabe et al.

(10) Patent No.: US 8,834,469 B2
(45) Date of Patent: Sep. 16, 2014

(54) ORTHOPAEDIC IMPLANT AND FASTENER ASSEMBLY

(75) Inventors: Kohsuke Watanabe, Memphis, TN (US); Roy W. Sanders, Tampa, FL (US)

(73) Assignee: Smith & Nephew, Inc., Memphis, TN (US)

(*) Notice: Subject to any disclaimer, the term of this patent is extended or adjusted under 35 U.S.C. 154(b) by 28 days.

(21) Appl. No.: 13/380,438

(22) PCT Filed: Jun. 30, 2010

(86) PCT No.: PCT/US2010/040631
§ 371 (c)(1),
(2), (4) Date: Feb. 23, 2012

(87) PCT Pub. No.: WO2011/002903
PCT Pub. Date: Jan. 6, 2011

(65) Prior Publication Data
US 2012/0143192 A1    Jun. 7, 2012

Related U.S. Application Data

(60) Provisional application No. 61/222,078, filed on Jun. 30, 2009.

(51) Int. Cl.
| | |
|---|---|
| A61B 17/56 | (2006.01) |
| A61B 17/58 | (2006.01) |
| A61F 2/30 | (2006.01) |
| A61B 17/72 | (2006.01) |
| A61B 17/74 | (2006.01) |
| A61B 17/80 | (2006.01) |

(52) U.S. Cl.
CPC ......... *A61B 17/7233* (2013.01); *A61B 17/744* (2013.01); *A61B 17/7266* (2013.01); *A61B 17/746* (2013.01); *A61B 17/8061* (2013.01); *A61B 17/7225* (2013.01); *A61B 17/725* (2013.01); *A61B 17/7283* (2013.01)
USPC ........................................................ 606/64

(58) Field of Classification Search
USPC ..................................................... 606/62–68
See application file for complete search history.

(56) References Cited

U.S. PATENT DOCUMENTS

| | | | |
|---|---|---|---|
| 2,267,925 | A | 12/1941 | Johnston |
| 2,699,774 | A | 1/1955 | Livingston |
| (Continued) | | | |

FOREIGN PATENT DOCUMENTS

| | | |
|---|---|---|
| AU | 199728574 | 7/1997 |
| AU | 200032139 | 8/2000 |
| (Continued) | | |

OTHER PUBLICATIONS

Baixauli, et al., "A Reinforced Rigid Fixation Device for Unstable Intertrochanteric Fractures," Clin. Ortho, 1(361):205-215 (Apr. 1999).

(Continued)

*Primary Examiner* — Mary Hoffman
*Assistant Examiner* — Michelle C Eckman
(74) *Attorney, Agent, or Firm* — Fish & Richardson P.C.

(57) ABSTRACT

Treating fractures using one or both of an implant, such as an intramedullary nail, and a fastening assembly, such as a lag screw and compression screw assembly. The implant in some implementations has a proximal section with a transverse aperture having a non-circular cross-section that may be shaped to selectively constrain the fastening assembly within the transverse aperture. Two or more components of the fastening assembly may be received to slide, in a controlled way, in the transverse aperture of the implant, and to cooperate to resist a force moment applied thereto.

34 Claims, 27 Drawing Sheets

(56) References Cited

U.S. PATENT DOCUMENTS

| | | | |
|---|---|---|---|
| 3,374,786 A | 3/1968 | Callender | |
| 3,530,854 A | 9/1970 | Kearney | |
| 3,630,261 A | 12/1971 | Gley | |
| 3,990,438 A | 11/1976 | Pritchard | |
| 4,103,683 A | 8/1978 | Neufeld | |
| 4,172,452 A | 10/1979 | Forte | |
| 4,432,358 A | 2/1984 | Fixel | |
| 4,438,762 A | 3/1984 | Kyle | |
| 4,484,570 A | 11/1984 | Sutter et al. | |
| 4,612,920 A | 9/1986 | Lower | |
| 4,621,629 A | 11/1986 | Koeneman | |
| 4,622,959 A * | 11/1986 | Marcus | 606/64 |
| 4,641,640 A | 2/1987 | Griggs | |
| 4,657,001 A | 4/1987 | Fixel | |
| 4,776,330 A | 10/1988 | Chapman | |
| 4,827,917 A | 5/1989 | Brumfield | |
| 4,978,349 A | 12/1990 | Frigg | |
| 5,007,910 A | 4/1991 | Anapliotis | |
| 5,032,125 A | 7/1991 | Durham | |
| 5,041,114 A | 8/1991 | Chapman | |
| 5,041,116 A | 8/1991 | Wilson | |
| 5,100,404 A | 3/1992 | Hayes | |
| 5,112,333 A | 5/1992 | Fixel | |
| 5,122,141 A | 6/1992 | Simpson et al. | |
| 5,167,663 A | 12/1992 | Brumfield | |
| 5,176,681 A | 1/1993 | Lawes et al. | |
| 5,190,544 A | 3/1993 | Chapman | |
| 5,269,784 A | 12/1993 | Mast | |
| 5,312,406 A | 5/1994 | Brumfield | |
| 5,324,292 A | 6/1994 | Meyers | |
| 5,364,398 A | 11/1994 | Chapman | |
| 5,364,399 A | 11/1994 | Lowery | |
| 5,429,640 A | 7/1995 | Shuler | |
| 5,429,641 A | 7/1995 | Gotfried | |
| 5,454,813 A | 10/1995 | Lawes | |
| 5,514,137 A | 5/1996 | Coutts | |
| 5,514,138 A | 5/1996 | McCarthy | |
| 5,531,748 A | 7/1996 | De la Caffiniere | |
| 5,549,610 A * | 8/1996 | Russell et al. | 606/64 |
| 5,562,666 A | 10/1996 | Brumfield | |
| 5,562,667 A | 10/1996 | Shuler | |
| 5,573,536 A | 11/1996 | Grosse | |
| 5,591,168 A | 1/1997 | Judet | |
| 5,653,709 A | 8/1997 | Frigg | |
| 5,658,288 A | 8/1997 | Kim | |
| 5,690,640 A | 11/1997 | Gotfried | |
| 5,713,902 A | 2/1998 | Friedl | |
| 5,741,256 A | 4/1998 | Bresina | |
| 5,743,908 A | 4/1998 | Kim | |
| 5,743,912 A | 4/1998 | Lahille | |
| 5,749,872 A | 5/1998 | Kyle | |
| 5,772,662 A | 6/1998 | Chapman | |
| 5,779,704 A | 7/1998 | Kim | |
| 5,810,821 A | 9/1998 | Vandewalle | |
| 5,855,579 A | 1/1999 | James | |
| 5,888,204 A | 3/1999 | Ralph et al. | |
| 5,908,422 A | 6/1999 | Bresina | |
| 5,928,235 A | 7/1999 | Friedl | |
| 5,954,722 A | 9/1999 | Bono | |
| 5,984,970 A | 11/1999 | Bramlet | |
| 6,059,786 A | 5/2000 | Jackson | |
| 6,077,264 A | 6/2000 | Chemello | |
| 6,102,913 A | 8/2000 | Jackson | |
| 6,106,528 A | 8/2000 | Durham | |
| 6,123,708 A | 9/2000 | Kilpela | |
| 6,126,661 A | 10/2000 | Faccioli | |
| 6,139,552 A | 10/2000 | Horiuchi | |
| 6,168,595 B1 | 1/2001 | Durham | |
| 6,183,474 B1 | 2/2001 | Bramlet | |
| 6,187,007 B1 | 2/2001 | Frigg | |
| 6,221,074 B1 | 4/2001 | Cole | |
| 6,228,085 B1 | 5/2001 | Theken | |
| 6,228,086 B1 | 5/2001 | Wahl et al. | |
| 6,235,031 B1 | 5/2001 | Hodgeman | |
| 6,235,033 B1 | 5/2001 | Brace et al. | |
| 6,261,290 B1 | 7/2001 | Friedl | |
| 6,270,499 B1 | 8/2001 | Leu et al. | |
| 6,281,290 B1 | 8/2001 | Klosiewicz | |
| 6,322,591 B1 | 11/2001 | Ahrens | |
| 6,406,477 B1 * | 6/2002 | Fujiwara | 606/67 |
| 6,409,768 B1 | 6/2002 | Tepic | |
| 6,413,259 B1 | 7/2002 | Lyons | |
| 6,423,066 B1 | 7/2002 | Harder et al. | |
| 6,443,954 B1 | 9/2002 | Bramlet et al. | |
| 6,461,360 B1 | 10/2002 | Adam | |
| 6,468,278 B1 | 10/2002 | Muckter | |
| 6,475,242 B1 | 11/2002 | Bramlet | |
| 6,511,481 B2 | 1/2003 | Von Hoffmann | |
| 6,524,314 B1 | 2/2003 | Dean et al. | |
| 6,533,788 B1 | 3/2003 | Orbay | |
| 6,533,789 B1 | 3/2003 | Hall, IV | |
| 6,562,042 B2 | 5/2003 | Nelson | |
| 6,565,573 B1 | 5/2003 | Ferrante | |
| 6,569,165 B2 | 5/2003 | Wahl | |
| 6,575,975 B2 | 6/2003 | Brace et al. | |
| 6,645,209 B2 | 11/2003 | Hall et al. | |
| 6,648,889 B2 | 11/2003 | Bramlet | |
| 6,652,529 B2 | 11/2003 | Swanson | |
| 6,669,701 B2 | 12/2003 | Steiner et al. | |
| 6,695,844 B2 | 2/2004 | Bramlet | |
| 6,719,759 B2 | 4/2004 | Wagner | |
| 6,755,832 B2 | 6/2004 | Happonen et al. | |
| 6,902,567 B2 | 6/2005 | Del Medico | |
| 6,905,500 B2 | 6/2005 | Jeon et al. | |
| 6,932,818 B2 | 8/2005 | Behrens | |
| 6,932,819 B2 | 8/2005 | Wahl et al. | |
| 7,135,023 B2 | 11/2006 | Watkins et al. | |
| 7,354,441 B2 | 4/2008 | Frigg | |
| 7,503,919 B2 | 3/2009 | Shaw | |
| 7,527,627 B2 * | 5/2009 | Ferrante et al. | 606/64 |
| 7,534,244 B2 * | 5/2009 | Ferrante et al. | 606/64 |
| 7,780,667 B2 * | 8/2010 | Watanabe et al. | 606/71 |
| 7,799,030 B2 * | 9/2010 | Watanabe et al. | 606/62 |
| 7,883,509 B2 * | 2/2011 | Ferrante et al. | 606/64 |
| 7,918,853 B2 * | 4/2011 | Watanabe et al. | 606/64 |
| 7,931,652 B2 | 4/2011 | Ferrante et al. | |
| 7,976,570 B2 | 7/2011 | Wagner et al. | |
| 8,100,911 B2 * | 1/2012 | Yamazaki et al. | 606/65 |
| 8,105,326 B2 * | 1/2012 | Ferrante et al. | 606/64 |
| 8,114,078 B2 | 2/2012 | Aschmann | |
| 8,172,841 B2 | 5/2012 | Defossez | |
| 8,187,275 B2 * | 5/2012 | Ferrante et al. | 606/64 |
| 8,298,234 B2 * | 10/2012 | Ferrante et al. | 606/64 |
| 8,449,544 B2 * | 5/2013 | Grusin | 606/64 |
| 2001/0012939 A1 | 8/2001 | Wahl et al. | |
| 2001/0037112 A1 | 11/2001 | Brace et al. | |
| 2002/0029041 A1 | 3/2002 | Hover et al. | |
| 2002/0032445 A1 * | 3/2002 | Fujiwara | 606/67 |
| 2002/0072748 A1 | 6/2002 | Robioneck | |
| 2002/0099379 A1 | 7/2002 | Adam | |
| 2002/0107578 A1 | 8/2002 | Speitling | |
| 2002/0111629 A1 | 8/2002 | Phillips | |
| 2002/0133156 A1 | 9/2002 | Cole | |
| 2002/0143334 A1 | 10/2002 | Hoffmann | |
| 2002/0143338 A1 | 10/2002 | Orbay et al. | |
| 2002/0151898 A1 | 10/2002 | Sohngen | |
| 2002/0156473 A1 | 10/2002 | Bramlet | |
| 2002/0161370 A1 | 10/2002 | Frigg et al. | |
| 2003/0004514 A1 | 1/2003 | Frigg et al. | |
| 2003/0018335 A1 | 1/2003 | Michelson | |
| 2003/0018336 A1 | 1/2003 | Vandewalle | |
| 2003/0069582 A1 | 4/2003 | Culber | |
| 2003/0074000 A1 | 4/2003 | Roth et al. | |
| 2003/0114855 A1 | 6/2003 | Wahl et al. | |
| 2003/0195515 A1 | 10/2003 | Sohngen | |
| 2004/0010252 A1 | 1/2004 | Zander et al. | |
| 2004/0010255 A1 | 1/2004 | Warburton | |
| 2004/0127898 A1 | 7/2004 | Adam | |
| 2004/0220566 A1 | 11/2004 | Bray | |
| 2005/0010223 A1 | 1/2005 | Gotfried | |
| 2005/0055024 A1 * | 3/2005 | James et al. | 606/64 |
| 2005/0069397 A1 | 3/2005 | Shavit | |
| 2005/0070902 A1 | 3/2005 | Medoff | |
| 2005/0101959 A1 | 5/2005 | Mitkovic | |

(56) References Cited

U.S. PATENT DOCUMENTS

| | | | |
|---|---|---|---|
| 2005/0131411 A1 | 6/2005 | Culbert | |
| 2005/0143739 A1 | 6/2005 | Shinjo | |
| 2005/0149024 A1* | 7/2005 | Ferrante et al. | 606/62 |
| 2005/0149025 A1* | 7/2005 | Ferrante et al. | 606/62 |
| 2005/0177158 A1 | 8/2005 | Doubler | |
| 2005/0234457 A1 | 10/2005 | James | |
| 2005/0273103 A1 | 12/2005 | Wahl | |
| 2006/0036248 A1 | 2/2006 | Ferrante | |
| 2006/0069392 A1 | 3/2006 | Renzi Brivio | |
| 2006/0084999 A1* | 4/2006 | Aschmann | 606/64 |
| 2006/0095039 A1* | 5/2006 | Mutchler | 606/64 |
| 2006/0100623 A1 | 5/2006 | Pennig | |
| 2006/0106384 A1 | 5/2006 | Reber et al. | |
| 2006/0106385 A1 | 5/2006 | Pennig | |
| 2006/0122600 A1 | 6/2006 | Cole | |
| 2006/0149247 A1 | 7/2006 | Frigg et al. | |
| 2006/0264949 A1 | 11/2006 | Kohut et al. | |
| 2006/0293668 A1 | 12/2006 | May et al. | |
| 2007/0055251 A1 | 3/2007 | Huebner | |
| 2007/0123873 A1* | 5/2007 | Czartoski et al. | 606/62 |
| 2007/0162011 A1 | 7/2007 | Leyden | |
| 2007/0270845 A1* | 11/2007 | Watanabe et al. | 606/62 |
| 2007/0270846 A1 | 11/2007 | Metzinger | |
| 2007/0288017 A1 | 12/2007 | Kaup | |
| 2007/0299447 A1* | 12/2007 | Watanabe et al. | 606/69 |
| 2008/0004623 A1* | 1/2008 | Ferrante et al. | 606/62 |
| 2008/0033430 A1* | 2/2008 | Ferrante et al. | 606/60 |
| 2008/0051790 A1 | 2/2008 | Defossez | |
| 2008/0119855 A1 | 5/2008 | Hoegerle | |
| 2008/0119856 A1 | 5/2008 | Gotfried | |
| 2008/0183171 A1* | 7/2008 | Elghazaly et al. | 606/64 |
| 2008/0188853 A1* | 8/2008 | Ferrante et al. | 606/62 |
| 2008/0195098 A1 | 8/2008 | Gotfried | |
| 2008/0269752 A1 | 10/2008 | Simon et al. | |
| 2008/0281326 A1* | 11/2008 | Watanabe et al. | 606/62 |
| 2008/0294164 A1* | 11/2008 | Frank et al. | 606/64 |
| 2009/0088768 A1 | 4/2009 | Grant et al. | |
| 2009/0209961 A1* | 8/2009 | Ferrante et al. | 606/62 |
| 2009/0248025 A1* | 10/2009 | Haidukewych et al. | 606/67 |
| 2009/0306666 A1* | 12/2009 | Czartoski et al. | 606/64 |
| 2010/0268229 A1* | 10/2010 | Siravo et al. | 606/64 |
| 2010/0331843 A1* | 12/2010 | Grusin | 606/64 |
| 2011/0060337 A1* | 3/2011 | Ferrante et al. | 606/64 |
| 2011/0087228 A1* | 4/2011 | Ferrante et al. | 606/64 |
| 2011/0196372 A1 | 8/2011 | Murase | |
| 2011/0238121 A1* | 9/2011 | Watanabe et al. | 606/289 |

FOREIGN PATENT DOCUMENTS

| | | |
|---|---|---|
| AU | 2006252075 | 7/2007 |
| AU | 2008201469 | 10/2008 |
| BE | 551875 | 11/1956 |
| DE | 29811670 | 9/1998 |
| DE | 19723339 | 12/1998 |
| DE | 19829228 | 10/1999 |
| EP | 0257118 | 3/1988 |
| EP | 0321170 | 6/1989 |
| EP | 0355411 | 2/1990 |
| EP | 0441577 | 8/1991 |
| EP | 0551846 | 7/1993 |
| EP | 0586824 | 3/1994 |
| EP | 0640318 | 3/1995 |
| EP | 0486483 | 2/1996 |
| EP | 0853923 | 7/1996 |
| EP | 0838199 | 4/1998 |
| EP | 0617927 | 1/1999 |
| EP | 0968685 | 1/2000 |
| EP | 1024762 | 8/2000 |
| EP | 0715832 | 1/2002 |
| EP | 1175872 | 1/2002 |
| EP | 1273271 | 6/2002 |
| EP | 1267734 | 2/2003 |
| EP | 1356777 | 10/2003 |
| EP | 1416868 | 5/2004 |
| EP | 1958580 | 8/2008 |
| EP | 1974682 | 10/2008 |
| EP | 1994903 | 11/2008 |
| FR | 2717674 | 3/1994 |
| FR | 2718013 | 10/1995 |
| FR | 2841459 | 1/2004 |
| FR | 2873913 | 2/2006 |
| GB | 2209947 | 6/1989 |
| JP | 2021859 | 1/1990 |
| JP | 08126650 | 5/1996 |
| JP | 09066060 | 3/1997 |
| JP | 09066061 | 3/1997 |
| JP | 10323351 | 12/1998 |
| JP | 2000515041 | 11/2000 |
| JP | 2002065687 | 3/2002 |
| JP | 2002253566 | 9/2002 |
| JP | 2003038508 | 2/2003 |
| JP | 2004089259 | 3/2004 |
| WO | WO 9526688 | 10/1995 |
| WO | WO 9708999 | 3/1997 |
| WO | WO 9718769 | 5/1997 |
| WO | WO 9737606 | 10/1997 |
| WO | WO 9802105 | 1/1998 |
| WO | WO 0139679 | 12/1999 |
| WO | WO 0076414 | 12/2000 |
| WO | WO 0156487 | 8/2001 |
| WO | WO 0178615 | 10/2001 |
| WO | WO 0191660 | 12/2001 |
| WO | WO 0134045 | 5/2002 |
| WO | WO 02058574 | 8/2002 |
| WO | WO 02078555 | 10/2002 |
| WO | WO 02085219 | 10/2002 |
| WO | WO 02085228 | 10/2002 |
| WO | WO 03015649 | 2/2003 |
| WO | WO 03022166 | 3/2003 |
| WO | WO 03028567 | 4/2003 |
| WO | WO 03032852 | 4/2003 |
| WO | WO 2004032726 | 4/2004 |
| WO | WO 2004110292 | 12/2004 |
| WO | WO 2005025436 | 3/2005 |
| WO | WO 2005025437 | 3/2005 |
| WO | WO 2005027764 | 3/2005 |
| WO | WO 2005034794 | 4/2005 |
| WO | WO 2006007553 | 1/2006 |
| WO | WO 2006040612 | 4/2006 |
| WO | WO 2006092593 | 9/2006 |
| WO | WO 2007038560 | 4/2007 |
| WO | WO 2007109302 | 9/2007 |
| WO | WO 2008022136 | 2/2008 |
| WO | WO 2008098728 | 8/2008 |
| WO | WO 2008128663 | 10/2008 |

OTHER PUBLICATIONS

Ballabarba, et al., Percutaneous Treatment of Peritrochanteric Fractures Using the Gamma Nail, Clin. Ortho., 375:30-42 (Apr. 1999).

Brochure entitled "OR manual PLATON (tantum) the medical people," 22 pages, Aug. 2002.

Brochure entitled Smith & Nephew Surgical Technique IMHS CP Clinically Proven Intramedullary Hip Screw, As Described by John Albert et al., pp. 1-34 (Mar. 2006).

Elder, et al., Biomechanical Evaluation of Calcium Phosphate Cernt-Augmented Fixation of Unstable Interochanteric Fractures, JOT, 14(6):386-393 (Aug. 2000).

International Search Report in related International Application No. PCT/US2007/006986.

Office Action mailed Jul. 3, 2008 in U.S. Appl. No. 10/937,075, 6 pages.

Roberts, et al., Second Generation Intramedullary Nailing of Subtrochanteric Femur Fractures: A Biomechanical Study of Fracture Site Motion, JOT, 16(4):231-238 (Apr. 2002).

Robinson, et al., Implant-Related Fractures of the Following Hip Fracture Surgery, JBJS, 84(7):1116 (2002).

Web page entitled, The PLATON-Locking-Nail System, numerous improvement, one page, Dec. 6, 2003.

Web page entitled The PLATON-Locking-Nail System: Quality without compromise, two pages, Jun. 30, 2003.

(56) References Cited

OTHER PUBLICATIONS

K. Kaspar et al., "Angle Stable Locking Reduces Interfragmentary Movements and Promotes Healing After Unreamed Nailing. Study of a Displaced Osteotomy Model in Sheet Tibiae," The Journal of Bone & Joint Surgery, 11 pages, Sep. 2005.
Office Action mailed Jan. 4, 2010 in U.S. Appl. No. 11/725,872, 34 pages.
Notice of Allowance and Fee(s) Due mailed Jun. 7, 2010 in U.S. Appl. No. 11/842,979, 12 pages.
Office Action mailed May 24, 2010 in U.S. Appl. No. 11/840,381, 16 pages.
Office Action mailed Apr. 23, 2010 in Japanese Patent Application No. 2006-525533, Summary translation, 2 pages.
Office Action mailed Aug. 31, 2010 in Japanese Patent Application No. 2006-525533, Summary translation, 2 pages.
Office Action for Canadian Application No. 2,536,049, mailed May 27, 2011, 2 pages.
Office Action for U.S. Appl. No. 12/494,860, mailed May 11, 2011, 22 pages.
Office Action for U.S. Appl. No. 12/494,860, mailed Dec. 6, 2011, 10 pages.
Office Action for U.S. Appl. No. 12/970,201, mailed Jan. 29, 2013.
International Search Report for International Application No. PCT/US2010/040631, mailed Feb. 28, 2011.
International Preliminary Report on Patentability for International Application No. PCT/US2010/040631, issued Jan. 4, 2012.
Notice of Reasons for Rejection for Japanese Application No. 2010-0237596, mailed Jun. 19, 2012.
Notice of Reasons for Rejection for Japanese Application No. 2010-0237596, mailed Dec. 11, 2012.

\* cited by examiner

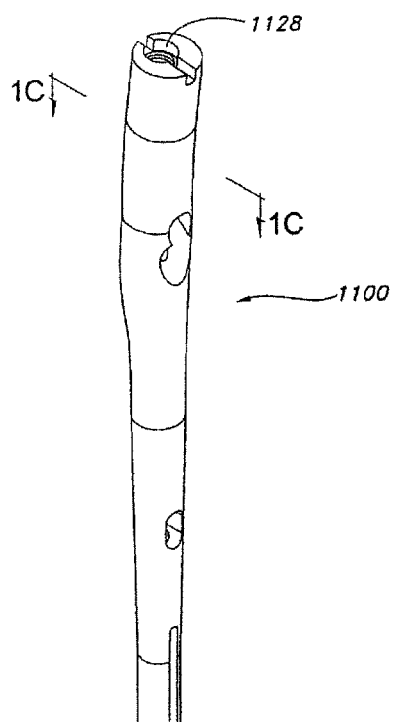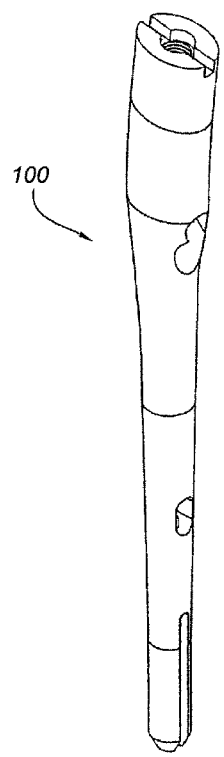
FIG. 1B          FIG. 1D
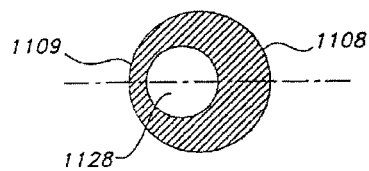
FIG. 1C

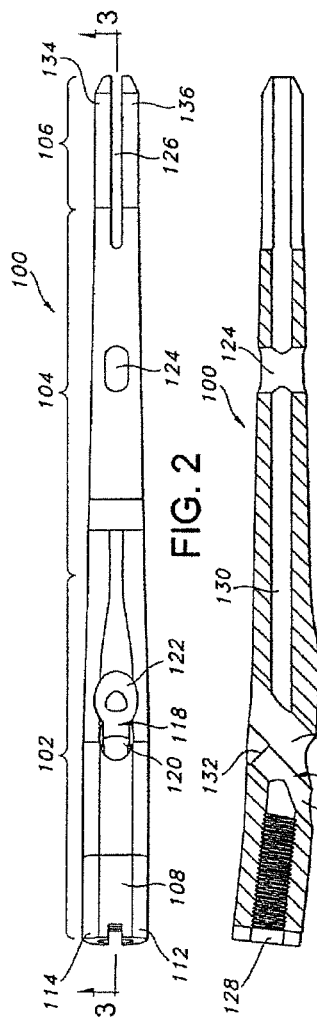
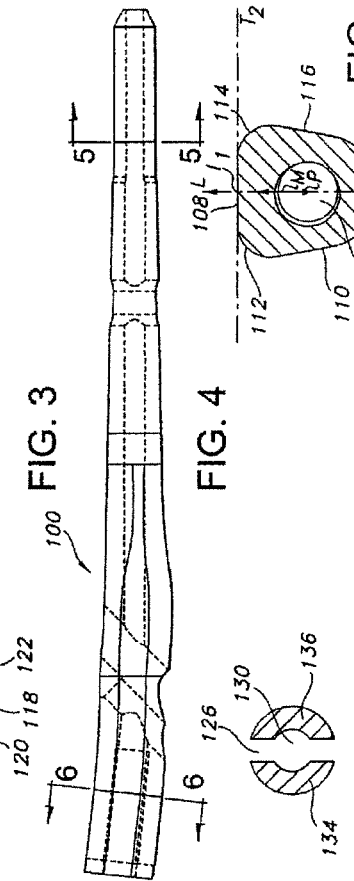
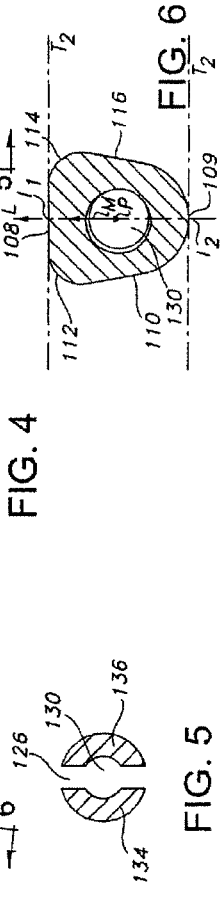
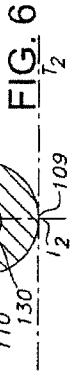

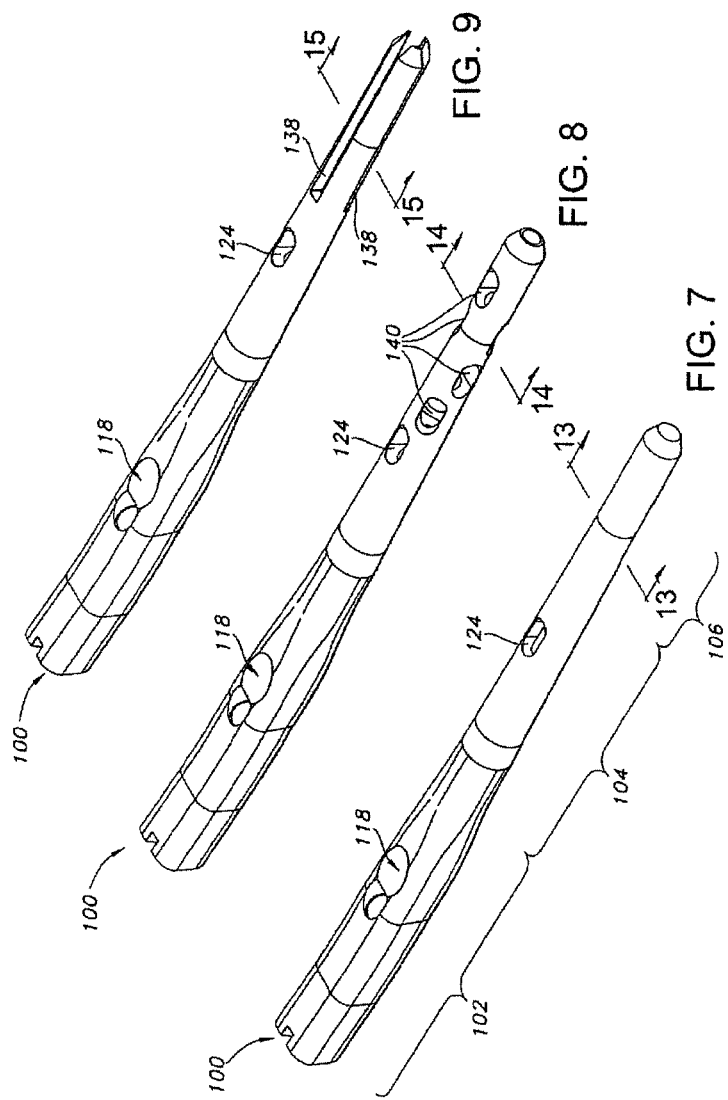

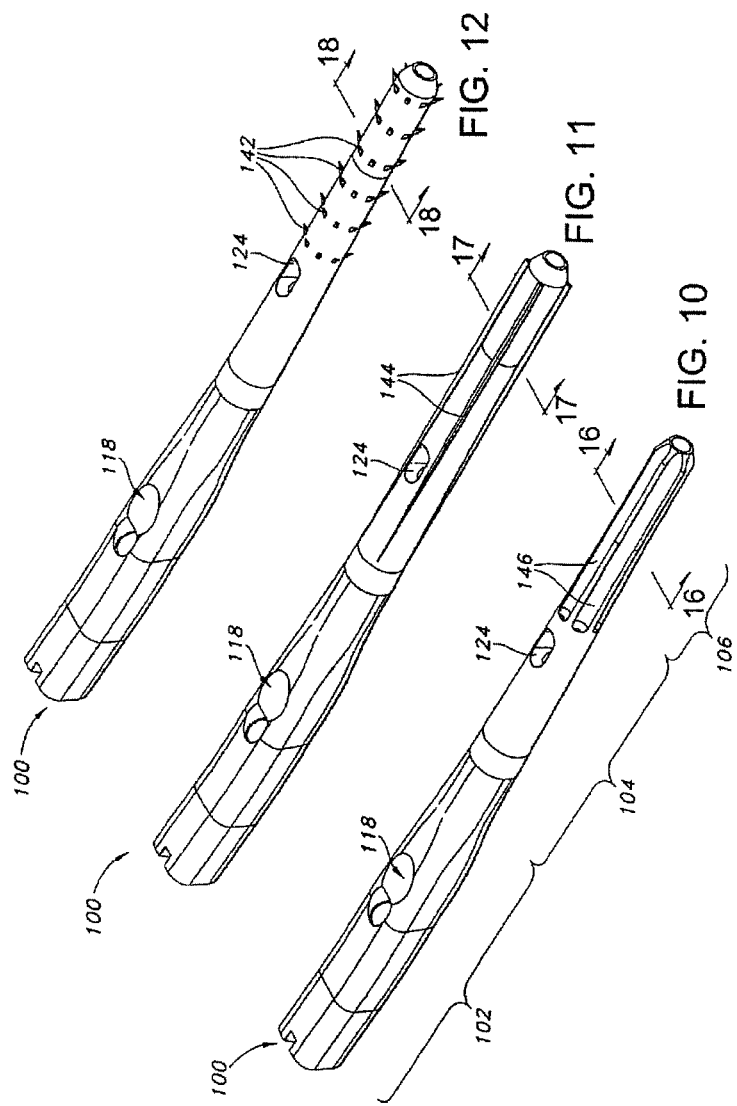

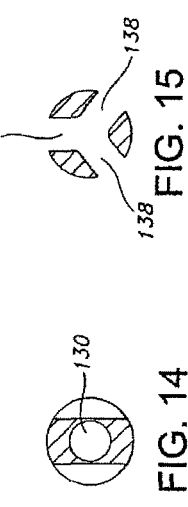
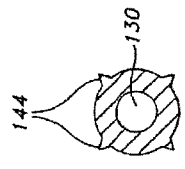
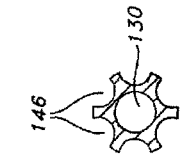

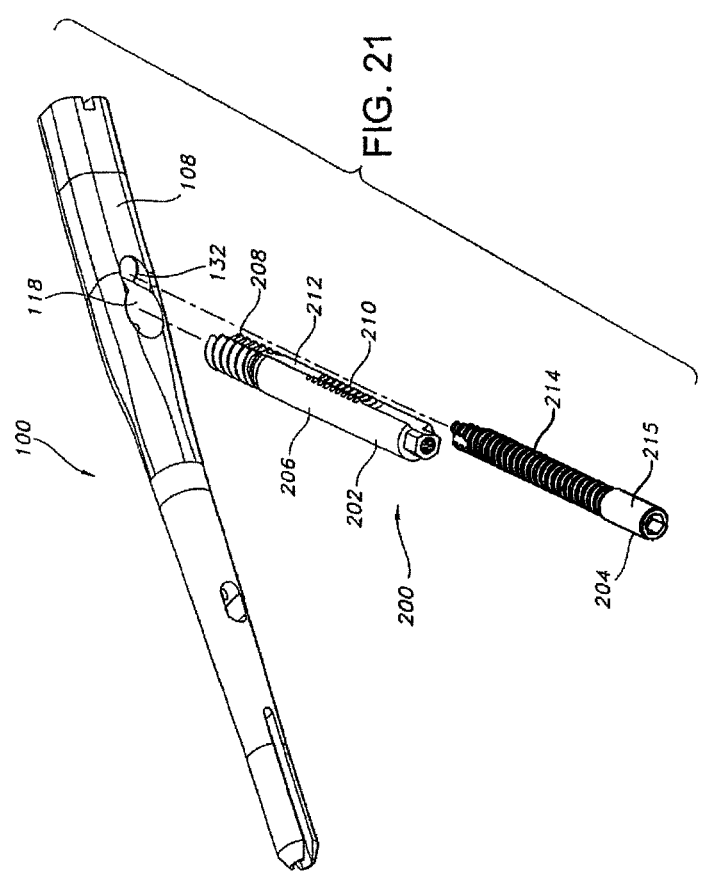

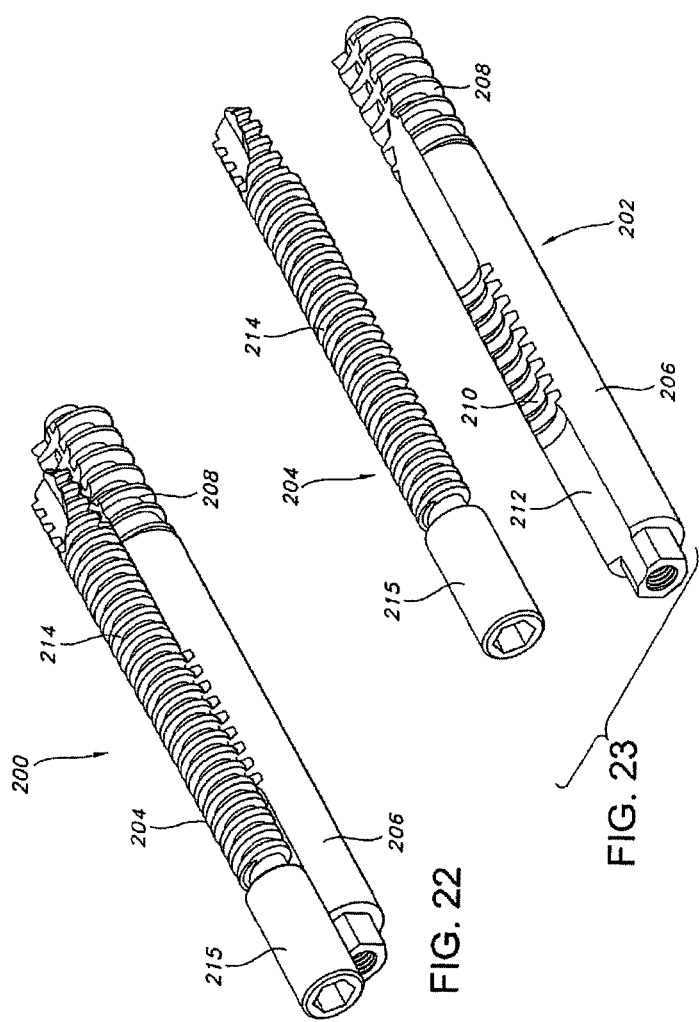

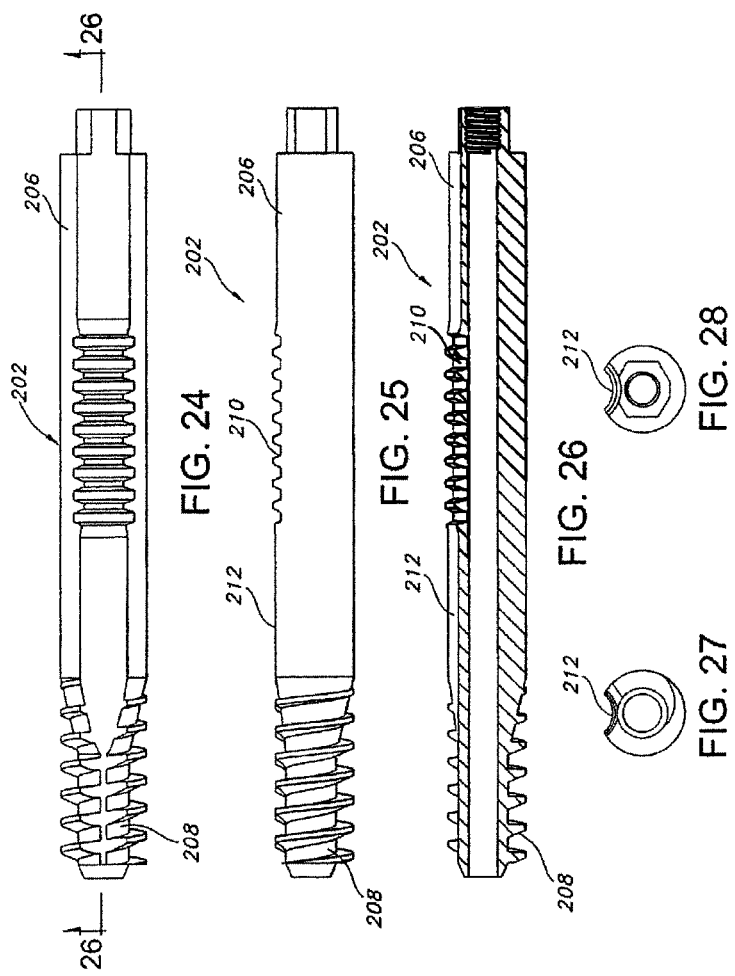

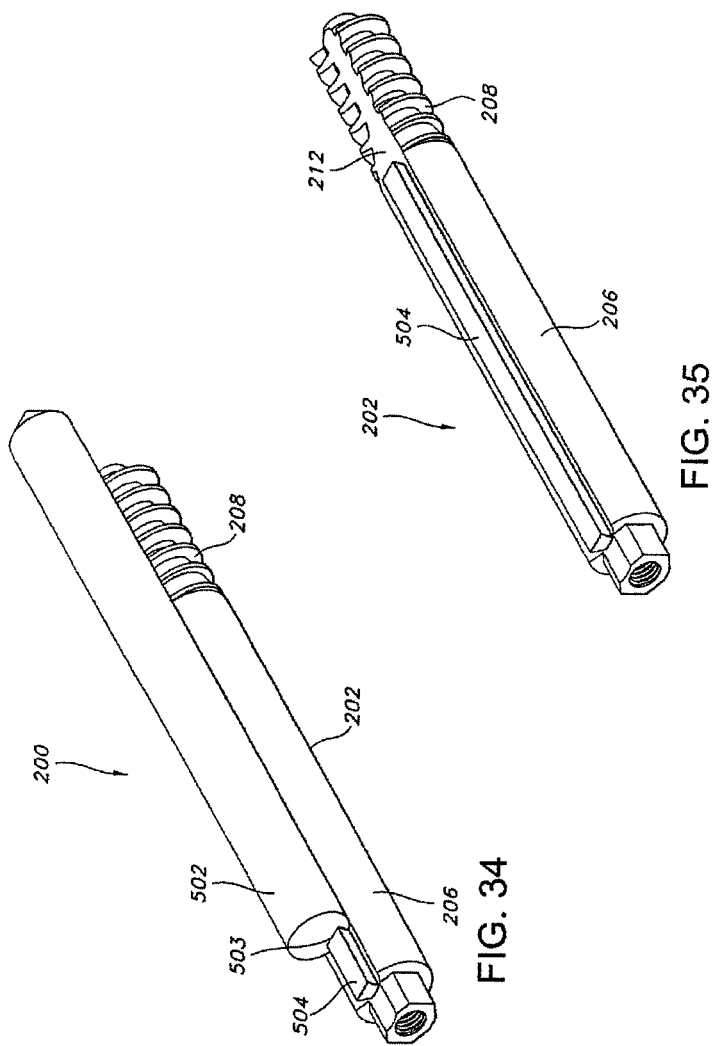

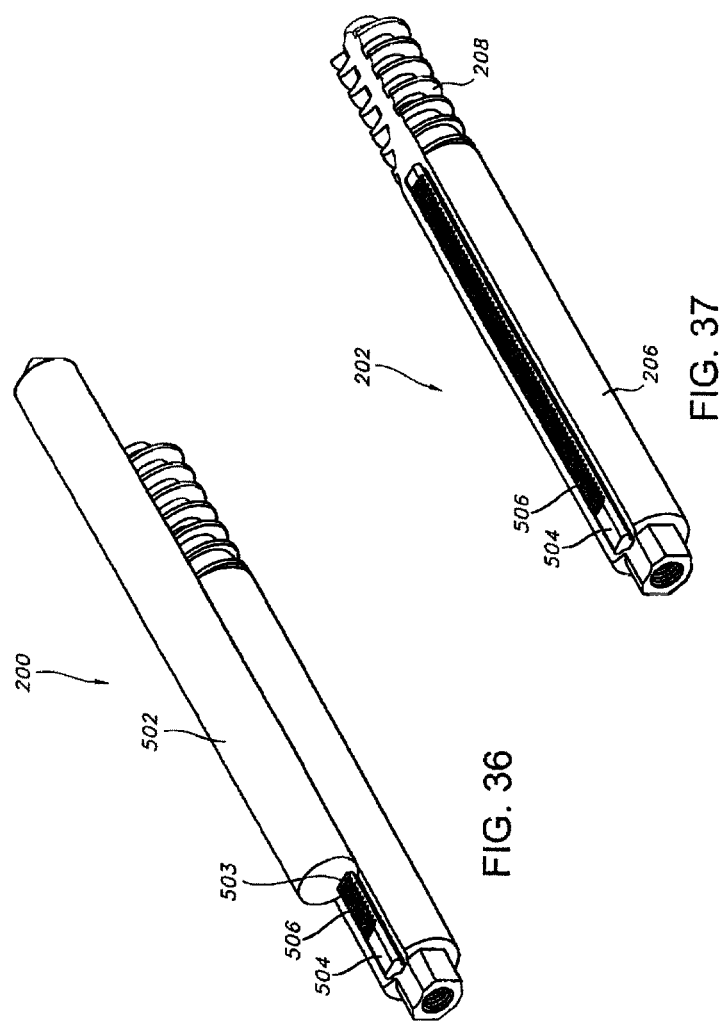

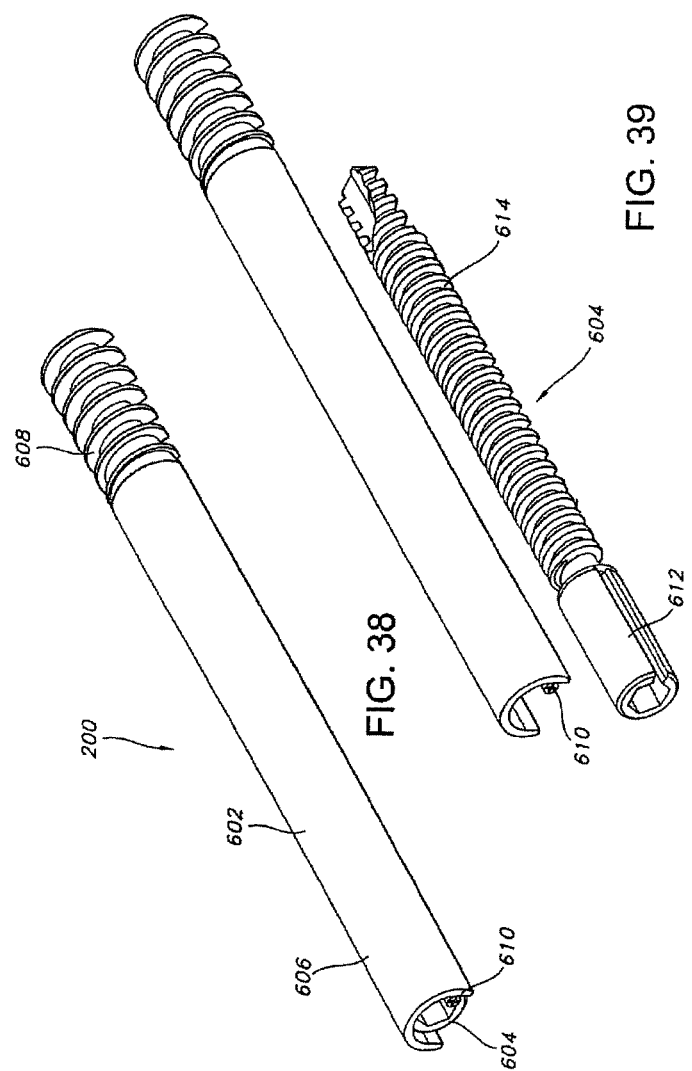

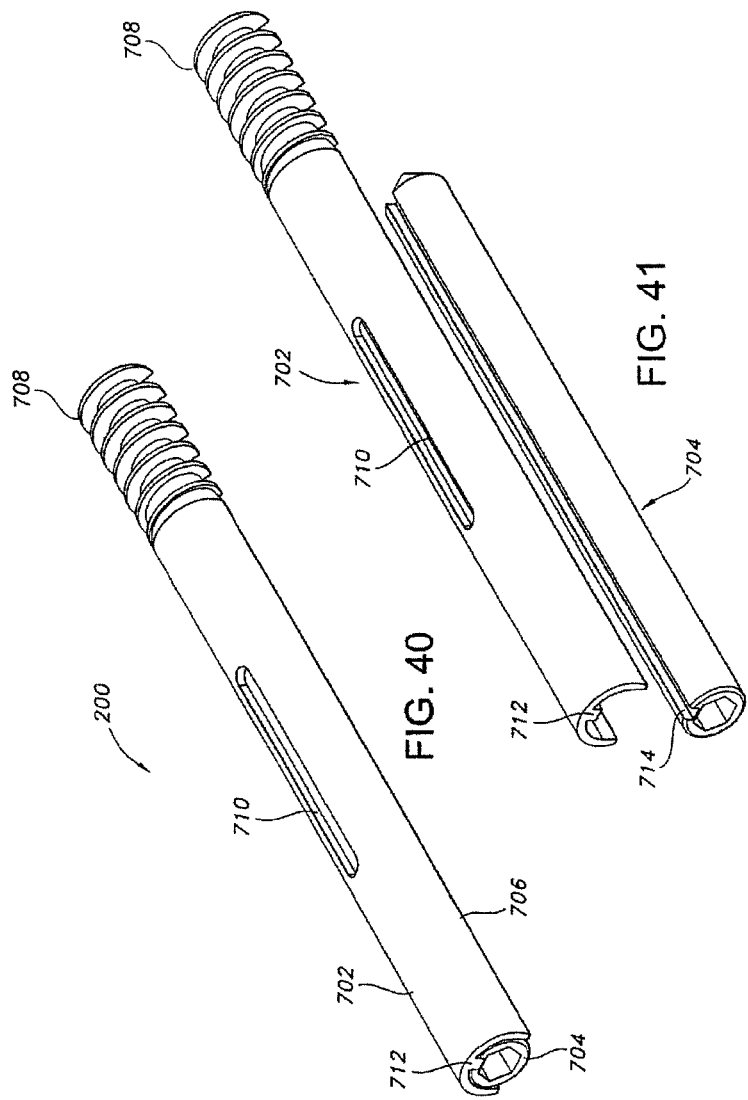

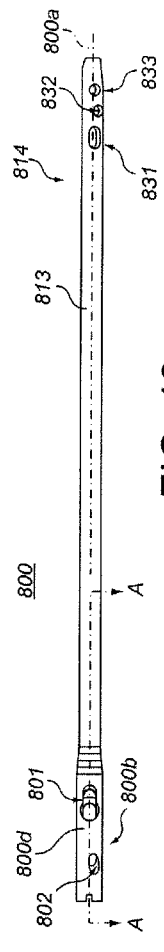
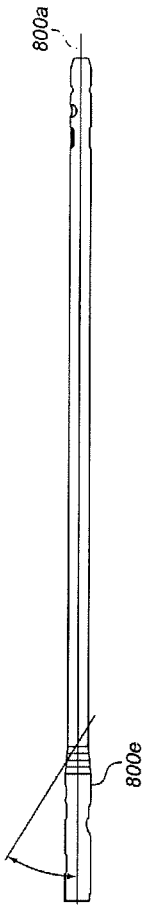
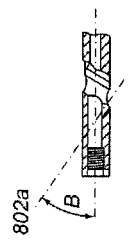
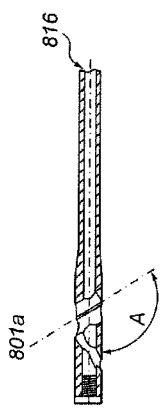
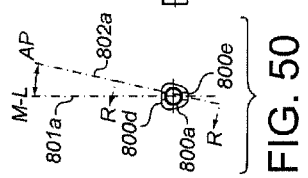

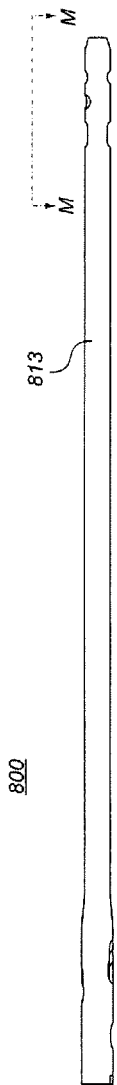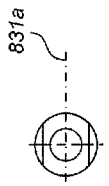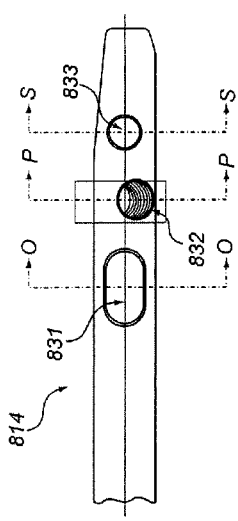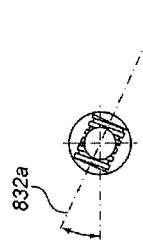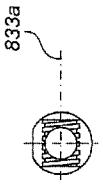
FIG. 53
FIG. 54
FIG. 55
FIG. 56
FIG. 57

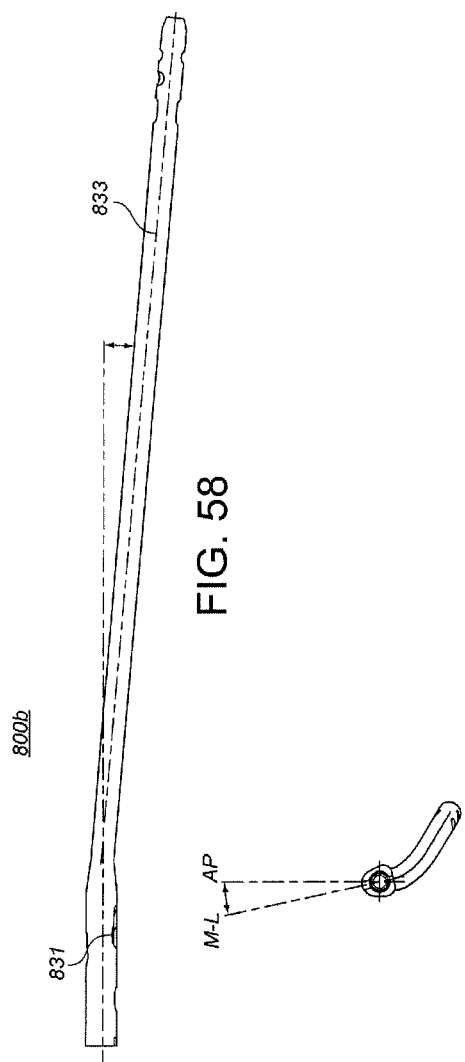
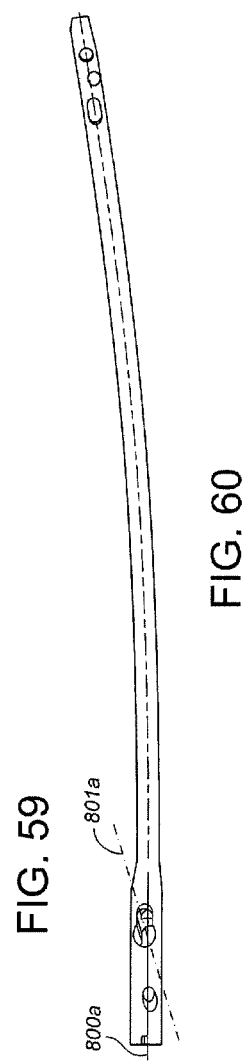
FIG. 58
FIG. 59
FIG. 60

ORTHOPAEDIC IMPLANT AND FASTENER ASSEMBLY

CROSS REFERENCE TO RELATED APPLICATION

This application claims priority to U.S. Provisional Patent Application Ser. No. 61/222,078, filed on Jun. 30, 2009, the entire contents of which are incorporated herein by reference.

BACKGROUND

1. Technical Field

This disclosure relates to orthopaedic implants and fastener assemblies.

2. Description of the Related Art

There are a variety of devices used to treat fractures of the femur, humerus, tibia, and other long bones. For example, fractures of the femoral neck, head, and intertrochanteric region have been successfully treated with a variety of compression screw assemblies, which include generally a compression plate having a barrel member, a lag screw and a compressing screw. Examples include the AMBI® and CLASSIC™ compression hip screw systems offered by Smith & Nephew, Inc. In such systems, the compression plate is secured to the exterior of the femur, and the barrel member is inserted in a predrilled hole in the direction of the femoral head. The lag screw has a threaded end, or another mechanism for engaging bone, and a smooth portion. The lag screw is inserted through the barrel member so that it extends across the break and into the femoral head. The threaded portion engages the femoral head. The compression screw connects the lag screw to the plate. By adjusting the tension of the compression screw, the compression (reduction) of the fracture can be varied. The smooth portion of the lag screw is free to slide through the barrel member to permit the adjustment of the compression screw. Some assemblies of the prior art use multiple screws to prevent rotation of the lag screw relative to the compression plate and barrel member and also to prevent rotation of the femoral head on the lag screw.

Intramedullary nails in combination with lag screws or other screw assemblies have been successfully used to treat fractures of the femur, humerus, tibia, and other long bones as well. A significant application of such devices has been the treatment of femoral fractures. One such nailing system is the IMHS® system offered by Smith & Nephew, Inc., and covered at least in part by U.S. Pat. No. 5,032,125 and various related international patents. Other seminal patents in the field include U.S. Pat. Nos. 4,827,917, 5,167,663, 5,312,406, and 5,562,666, which are all assigned to Smith & Nephew, Inc. These patents are all hereby incorporated by reference. A typical prior art intramedullary nail may have one or more transverse apertures through its distal end to allow distal bone screws or pins to be screwed or otherwise inserted through the femur at the distal end of the intramedullary nail. This is called "locking" and secures the distal end of the intramedullary nail to the femur. In addition, a typical intramedullary nail may have one or more apertures through its proximal end to allow a lag screw assembly to be screwed or otherwise inserted through the proximal end of the intramedullary nail and into the femur. The lag screw is positioned across the break in the femur and an end portion of the lag screw engages the femoral head. An intramedullary nail can also be used to treat shaft fractures of the femur or other long bones.

As with compression hip screw systems, intramedullary nail systems are sometimes designed to allow compression screws and/or lag screws to slide through the nail and thus permit contact between or among the bone fragments. Contact resulting from sliding compression facilitates faster healing in some circumstances. In some systems, two separate screws (or one screw and a separate pin) are used in order, among other things, to prevent rotation of the femoral head relative to the remainder of the femur, to prevent penetration of a single screw beyond the femoral head, and to prevent a single screw from tearing through the femoral neck and head. When an additional screw or pin is used, however, unequal forces applied to the separated screws or pins can cause the separate screws or pins to be pressed against the sides of the holes through which the separate screws or pins are intended to slide. This may result in binding, which reduces the sliding of the screws or pins through the nail. Conversely, a problem can result from excessive compression of the femoral head toward or into the fracture site. In extreme cases, excessive sliding compression may cause the femoral head to be compressed all the way into the trochanteric region of the femur.

SUMMARY

One or both of a structure configured to be implanted in or stabilize a first bone fragment and a fastening assembly can be used to treat bone fractures. The structure may take the form of a plate or other device for at least partial application to the outer surface of bone, or an implant for at least partial implantation within bone. Such implants may include a proximal section having a transverse aperture, and an aperture substantially along their length. Preferably, they include at least one cross-section in their proximal portions which features a shape that imparts additional strength and resistance to tension. Such shapes can be provided, for instance, by (1) adding additional mass in lateral portions of the cross section, and/or (2) strategically adding and reducing mass in the cross section to take advantage of flange effects similar to the way flanges add structural benefits to I-beams and channels. One way to characterize such cross-sections, which can but need not be asymmetrical with respect to at least one axis, is that they generally feature a moment of inertia extending in a lateral direction from a point that is the midpoint of a line from a lateral tangent to a medial tangent of the cross section. In some structures, that line is coplanar with the axis of the transverse aperture and coplanar with the cross section and thus defined by the intersection of those planes. The endpoints of that line can be defined as the intersection of the line with tangents to the medial aspect and the lateral aspect of the cross section, respectively. Such implants also typically include a distal section and a transition section that provides a coupling between the proximal section and the distal section.

Fastening assemblies can include an engaging member and a compression device. The fastening assemblies are adapted to be received in the transverse aperture of the implant in a sliding relationship, so that the fastening assembly is adapted to slide with respect to the transverse aperture, and thus apply compression to a fracture and for any other desired purpose. The engaging member is adapted to gain purchase in a second bone fragment. The engaging member and the compression device are configured so that the compression device interacts with a portion of the implant and also with a portion of the engaging member so that adjustment of the compression device controls sliding of the engaging member relative to the implant and thereby enables controlled movement between the first and second bone fragments. In some implementations, the compression device at least partially directly contacts the second bone fragment when implanted.

In one general aspect, a femoral intramedullary nail includes a shaft having a proximal region, a distal region, a medial side, a lateral side, and a longitudinal axis extending proximally and distally, the proximal region having a non-circular cross-sectional shape perpendicular to the longitudinal axis. A reconstruction aperture is located in the proximal region for receiving two members in a reconstruction mode and the aperture is oriented to target the femoral head and neck. An antegrade aperture is located in the proximal region for receiving a member in an antegrade mode. The antegrade aperture is oriented to target the lesser trochanter. The reconstruction aperture extends from the medial side to the lateral of the nail and the antegrade aperture is radially offset from the reconstruction aperture.

Implementations can include one or more of the following features. For example, the antegrade aperture includes an exit opening located within the reconstruction aperture. The reconstruction aperture comprises two overlapping apertures. The shaft comprises a head portion in the proximal region, the head portion having a cross-sectional shape perpendicular to the longitudinal axis that is different from a cross-sectional shape perpendicular to the longitudinal axis of the distal region of the shaft. The longitudinal axis within the head portion is angled from the longitudinal axis in the distal region.

In another general aspect, a femoral intramedullary nail includes a shaft having a proximal region, a distal region, a medial side, a lateral side, and a longitudinal axis extending proximally and distally. A reconstruction aperture is located in the proximal region for receiving two members in a reconstruction mode, and the reconstruction aperture is oriented to target the femoral head and neck. An antegrade aperture is located in the proximal region for receiving a member in an antegrade mode, and the antegrade aperture is oriented to target the lesser trochanter. A distal aperture is located in the distal region, and the reconstruction, antegrade, and distal apertures each have a central through axis. The central through axis of the antegrade aperture lies within an antegrade plane, with the antegrade plane being parallel to the longitudinal axis. The through axis of the distal aperture lies in the antegrade plane or a plane parallel to the antegrade plane, and the central through axis of the reconstruction aperture intersects the antegrade plane.

Implementations can include one or more of the following features. For example, the reconstruction aperture comprises two overlapping apertures. The reconstruction aperture comprises two discrete apertures. The shaft comprises a head portion in the proximal region, the head portion having a non-circular cross section perpendicular to the longitudinal axis. The longitudinal axis within the head portion is angled from the longitudinal axis in the distal region.

In another general aspect, an intramedullary nail includes a shaft having a proximal region, a distal region, a medial side, a lateral side, and a longitudinal axis extending proximally and distally. A reconstruction aperture is located in the proximal region for receiving two members in reconstruction mode, with the reconstruction aperture having an entry opening substantially on the lateral side of the shaft and an exit opening substantially on the medial side of the shaft. An antegrade aperture is located in the proximal region for receiving a member in an antegrade mode, with the antegrade aperture having an entry opening substantially on the lateral side of the shaft and an exit opening substantially on the medial side of the shaft. The antegrade aperture exit opening is contained entirely within the reconstruction aperture exit opening.

Implementations can include one or more of the following features. For example, the reconstruction aperture comprises two overlapping apertures. The reconstruction aperture comprises two discrete apertures. The shaft comprises a head portion in the proximal region, the head portion having a non-circular cross section perpendicular to the longitudinal axis. The longitudinal axis within the head portion is angled from the longitudinal axis in the distal region. A central through axis of the antegrade aperture intersects a plane that includes a central through axis of the reconstruction aperture.

In another general aspect, an intramedullary nail includes a first non-circular transverse aperture having a central through axis oriented off a central long axis of the nail, with the first transverse aperture including a shoulder and configured to receive a compression assembly. The first transverse aperture includes an entry on a lateral side of the nail and an exit on a medial side of the nail. A second transverse aperture has a central through axis oriented off the central long axis of the nail and has an entry on the lateral side of the nail and an exit on the medial side of the nail within the exit of the first transverse aperture. The central through axis of the second transverse aperture extends along an axis that is radially-offset from the central through axis of the first transverse aperture.

Implementations can include one or more of the following features. For example, the first transverse aperture and the second transverse aperture are located in a head, and a third transverse aperture is located proximate a distal end of the nail. The head is angled relative to the long axis. A bore extends in a direction of the long axis, with the bore intersecting the first transverse aperture.

In another general aspect, an orthopaedic implant includes a nail having a long axis, an inner wall defining a through hole oriented off the long axis, and a first transverse aperture proximal of the through hole. The inner wall includes a first semi-cylindrical section having an arc greater than 180 degrees and defines a first portion of the through to hole. A second U-shaped section has a pair of parallel walls and a semi-cylindrical segment having an arc of approximately 180 degrees. The second U-shape section defines a second portion of the through hole. The arc of the first semi-cylindrical section defines a first open face of the first portion of the through hole, and the parallel walls of the second U-shape portion define a second open face of the second portion of the through hole opposing the first open face, such that a cylindrical member of substantially the same diameter as that of the second semi-cylindrical section can pass out from the second portion of the through hole toward the first portion of the through hole.

Implementations can include one or more of the following features. For example, the first transverse aperture has an exit located in the inner wall. The first transverse aperture extends along an axis that is radially-offset from the orientation of the through hole. The nail further comprises a second transverse aperture located proximate a distal end of the nail. The second transverse aperture extends along an axis that is non-perpendicular to the long axis of the nail. The first transverse aperture is oriented off the long axis and has an entry located in a head of the nail, the head of the nail being angled relative to the long axis of the nail. A second transverse aperture is located proximate a distal end of the nail, the second transverse aperture having an opening aligned with the entry of the first proximal aperture.

BRIEF DESCRIPTION OF THE DRAWINGS

FIG. 1B is a perspective view of an intramedullary nail.

FIG. 1C is a cross-sectional view of a portion of the nail of FIG. 1B.

FIG. 1D is a perspective view of an intramedullary nail.

FIG. 2 is an elevation view of the intramedullary nail of FIG. 1.

FIG. 3 is a cross-section view of the intramedullary nail of FIG. 2 taken through the line 3-3.

FIG. 4 is a side view of the intramedullary nail of FIG. 2.

FIG. 5 is a cross-section view of the intramedullary nail of FIG. 4 taken through the line 5-5.

FIG. 6 is a cross-section of the intramedullary nail of FIG. 4 taken through the line 6-6.

FIGS. 7-12 are perspective views of intramedullary nails.

FIG. 13 is a cross-section view of the intramedullary nail of FIG. 7 taken through line 13-13.

FIG. 14 is a cross-section view of the intramedullary nail of FIG. 8 taken through line 14-14.

FIG. 15 is a cross-section view of the intramedullary nail of FIG. 9 taken through line 15-15.

FIG. 16 is a cross-section view of the intramedullary nail of FIG. 10 taken through line 16-16.

FIG. 17 is a cross-section view of the intramedullary nail of FIG. 11 taken through line 17-17.

FIG. 18 is a cross-section view of the intramedullary nail of FIG. 12 taken through line 18-18.

FIG. 21 is an exploded view of the intramedullary device and fastener assembly shown in FIG. 20.

FIG. 22 is a perspective view of the fastener assembly shown in FIG. 20.

FIG. 23 is an exploded view of the fastener assembly of FIG. 20.

FIG. 24 is an elevation view of the engaging member of the fastener assembly of FIG. 23.

FIG. 25 is a side view of the engaging member of FIG. 24.

FIG. 26 is a cross-section view of the engaging member of FIG. 24 taken through line 26-26.

FIG. 27 is an end view of one end of the engaging member of FIG. 24.

FIG. 28 is an end view of the other end of the engaging member of FIG. 24.

FIG. 34 is a perspective view of a fastener assembly.

FIG. 35 is a perspective view of the lag screw of the fastener assembly of FIG. 34.

FIG. 36 is a perspective view of a fastener assembly.

FIG. 37 is a perspective view of the lag screw of the fastener assembly of FIG. 36.

FIG. 38 is a perspective view of a fastener assembly.

FIG. 39 is an exploded view of the fastener assembly of FIG. 38.

FIG. 40 is a perspective view of a fastener assembly.

FIG. 41 is an exploded view of the fastener assembly of FIG. 40.

FIG. 48 is a plan view of a lateral side of an intramedullary nail.

FIG. 49 is side plan view of the intramedullary nail of FIG. 48.

FIG. 50 is a proximal end view of the intramedullary nail of FIG. 47.

FIG. 51 is a cross-sectional view of the intramedullary nail taken along lines A-A of FIG. 48 in the M-L plane of FIG. 50.

FIG. 52 is a cross-sectional view of the intramedullary nail taken along the AP plane of FIG. 50.

FIG. 53 is side plan view of the intramedullary nail of FIG. 47 perpendicular to the AP plane of FIG. 50.

FIG. 54 is a plan view of the lateral side of the distal end of the intramedullary nail taken along lines M-M of FIG. 53.

FIG. 55 is a cross-sectional view of the intramedullary nail taken along lines O-O of FIG. 54.

FIG. 56 is a cross-sectional view of the intramedullary nail taken along lines P-P of FIG. 54.

FIG. 57 is a cross-sectional view of the intramedullary nail taken along lines S-S of FIG. 54.

FIG. 58 is a side view of the intramedullary nail of FIGS. 47-57 perpendicular to the AP plane of FIG. 50 including bends.

FIG. 59 is an end view of the intramedullary nail of FIG. 58.

FIG. 60 is a plan view of the lateral side of the nail of FIG. 58.

DETAILED DESCRIPTION

Figure 1:
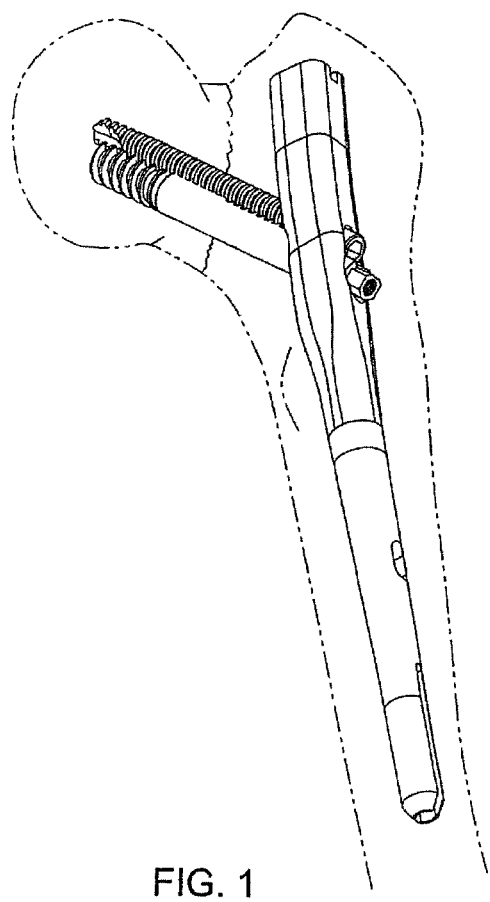
FIG. 1 is a perspective view of an intramedullary shown installed in a femur.

Methods, devices and systems according to implementations of this disclosure seek to provide improved treatment of femur fractures. FIGS. 1-6 illustrate various views of one implementation of an intramedullary nail 100. The intramedullary nail 100 has a longitudinal bore 130 throughout to aid in insertion in the bone. The intramedullary nail 100 has a proximal section 102, a transition section 104, and a distal section 106.

The proximal section 102 of the particular structure shown in FIGS. 1-6 preferably features an anatomically inspired shape that corresponds more accurately to typical cortical bone. One version of such shape is shown in the cross-sectional view of the proximal section 102 in FIG. 6. The particular cross-section of the proximal section 102 shown in FIG. 6 is generally non-circular and exists along at least some portions of the length of the intramedullary nail 100. The cross-section of FIG. 6 has a lateral side or aspect 108 that is larger than a medial side or aspect 109. The lateral side 108 and medial side 109 are joined by a first side 110 and a second side 116. At the intersection of the first side 110 with the lateral side 108 is a first radiused corner 112 and at the intersection of the second side 116 with the lateral side 108 is a second radiused corner 114. The first side 110, second side 116 and lateral side 108 are of approximately equal length. The first side 110 and second side 116 are oriented at acute angles relative to the lateral side 108, so that the medial side 109 is smaller than the lateral side 108. By having the lateral side 108 larger than the medial side 109 the rotational stability of the intramedullary nail 100 is increased, and resistance to bending and twisting can also be enhanced.

The medial side 109 shown in FIG. 6 can be radiused. As can be seen in FIG. 4, the radiused medial side 109 protrudes out from the transition section 104 and continues to the proximal end of the intramedullary nail 100. The protrusion of the medial side 109 corresponds to the calcar region of the femur and improves the evenness of load distribution between the bone and intramedullary nail 100.

Furthermore, the general cross-section geometry of the proximal section 102 reduces peak stresses in the proximal section 102. More specifically, the typical failure mode of an intramedullary nail and screw assembly combination is failure of the nail in tension on its lateral side. The tension is created by bending moment induced by body weight load that is applied to the screw assembly. Therefore, it would be beneficial in reducing stress in the proximal section of a nail to include more material on the side of the nail that is in tension, the lateral side, to shape the cross section more effectively to enhance strength and robustness in the lateral area, or both. The design illustrated in FIG. 6 accomplishes this objective. The lateral side 108 is wider than the medial side 109, thus imparting, at least partially, a flange-like effect. Stress per unit area induced on the lateral side 108 is less than would be the case if the lateral side featured a smaller cross-sectional area, such as the cross-sectional area of the medial side 109.

A structure according to another implementation of the disclosure that benefits from the same principle is shown in FIGS. 1B and 1C which illustrate an intramedullary nail 1100 with a generally circular cross section whose generally circular aperture 1128 is disposed other than concentric with the periphery of the cross section. In the particular structure shown in these two figures, the offset aperture 1128 is offset toward the medial side 1109 such that a greater portion of material is available to take load, and reduce stress, on the lateral side 1108. Likewise, any cross-section that provides more material on the lateral side of the section reduces stress per unit area in the nail on that side.

Figure 1A:
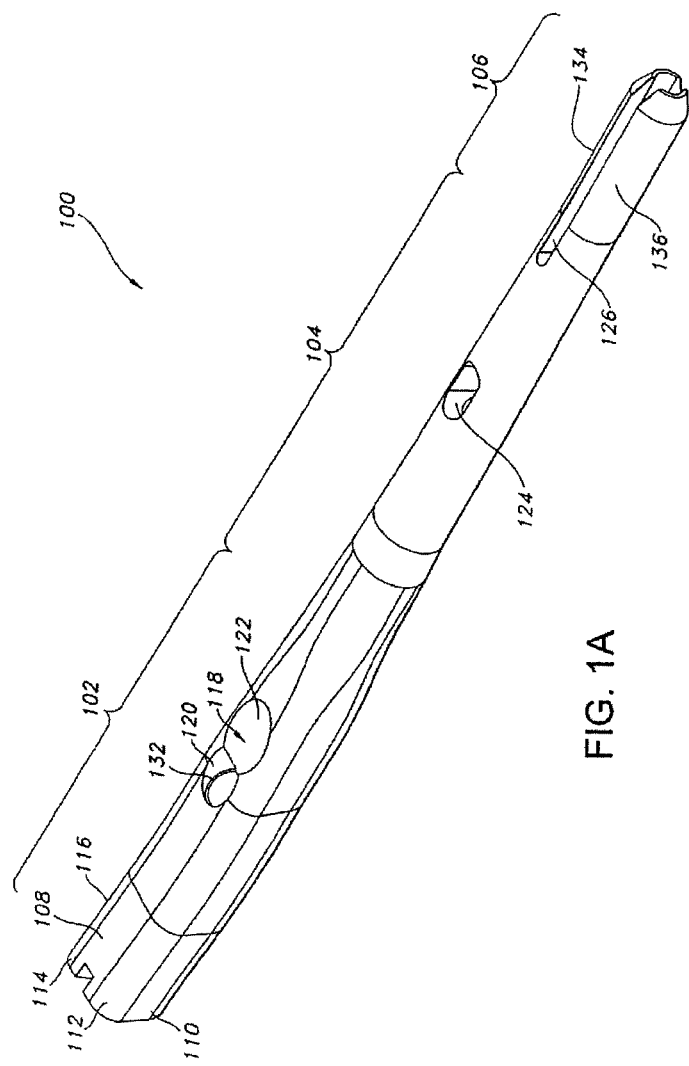
FIG. 1A is a perspective view of an intramedullary nail in greater detail.

Regardless of the particular manner in which material or mass may be added to some portions of the lateral parts of the cross section of proximal portion 102, material may be added and removed from some portions of the cross section in order to increase the strength and robustness of the lateral parts, or both, the effect can be characterized as imparting a moment of inertia to the cross section oriented at least partially in the direction of the lateral side or aspect 108. In a preferred implementation, the moment of inertia (shown denoted by the letter M on FIG. 6) can be characterized as extending in a lateral direction, or at least partially toward lateral aspect or side 108 from a point P that is the midpoint of a line L extending from the intersection I1 of that line with a tangent T1 to the lateral aspect 108, to the intersection I2 of that line with a tangent T2 to the medial aspect 109. Stated another way, the effect in at least some cases is to create a cross section that features a moment of inertia extending in at least partially lateral direction from a center of the cross section. Preferably, that center can be a midpoint between the lateral and medial edges of the cross section. Alternatively, that center can be the center of mass of the cross section. The radius of gyration reflected by the moment of inertia, which is a function of the square of the distance of the incremental mass from the center, reflects additional strength in lateral parts of the proximal portion 102 caused by more mass or more strategically placed mass in the cross section. In some structures, line L is coplanar with the axis of the longitudinal bore 130 and coplanar with the plane of the cross section and thus defined by the intersection of those planes. As FIG. 1A, on the one hand, and 1B and 1C on the other hand reflect, and bearing in mind that these are only two of a myriad of structures that can impart such lateral additional strength and robustness, the cross section can but need not be asymmetrical with respect to at least one of its axes. Additionally, the longitudinal bore 130 can be located to share its central axis with a geometric center of the cross section, or it can be offset in order to help impart the lateral strength or for other purposes.

In the particular device shown in FIGS. 1-6, the first side 110, second side 116 and lateral side 108 have flat portions. Alternatively, these sides could be curved. In the implementations shown in FIGS. 1-6, the medial side 109 is radiused, but as one skilled in the art could appreciate, the medial side could be flat or have one or more flat portions.

Figure 33:
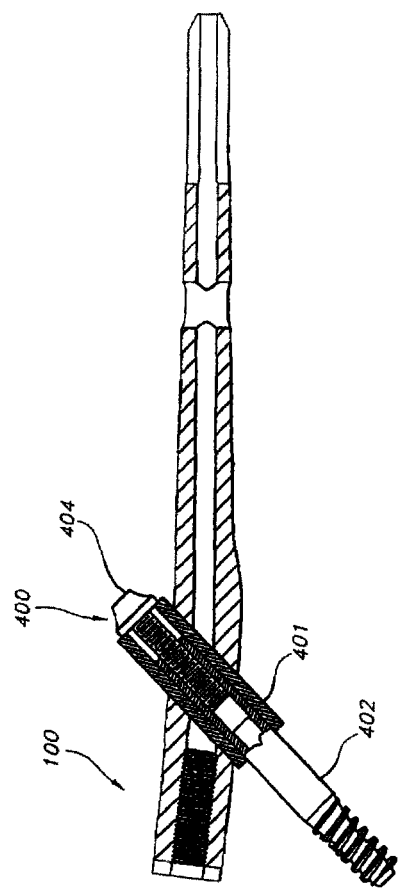
FIG. 33 is a cross-section view of an intramedullary nail and screw assembly.
Figure 45:
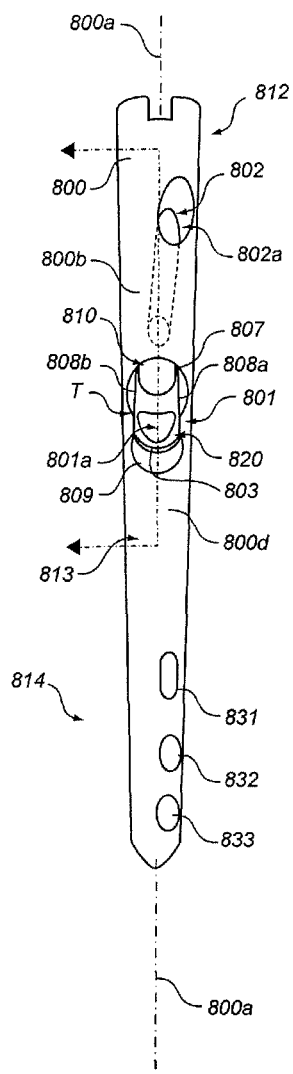
FIG. 45 is a perspective view showing a lateral side of an intramedullary nail.
Figure 46:
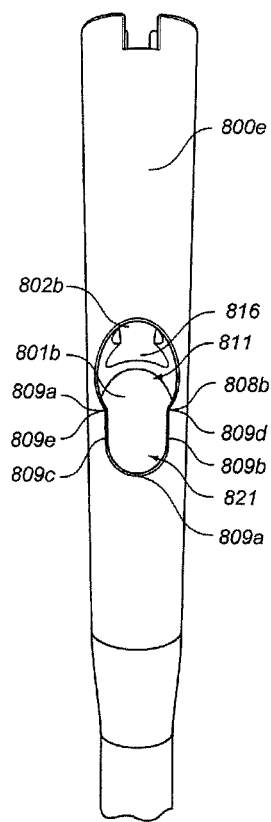
FIG. 46 is a perspective view showing a medial side of the intramedullary nail of FIG. 45.
Figure 47:
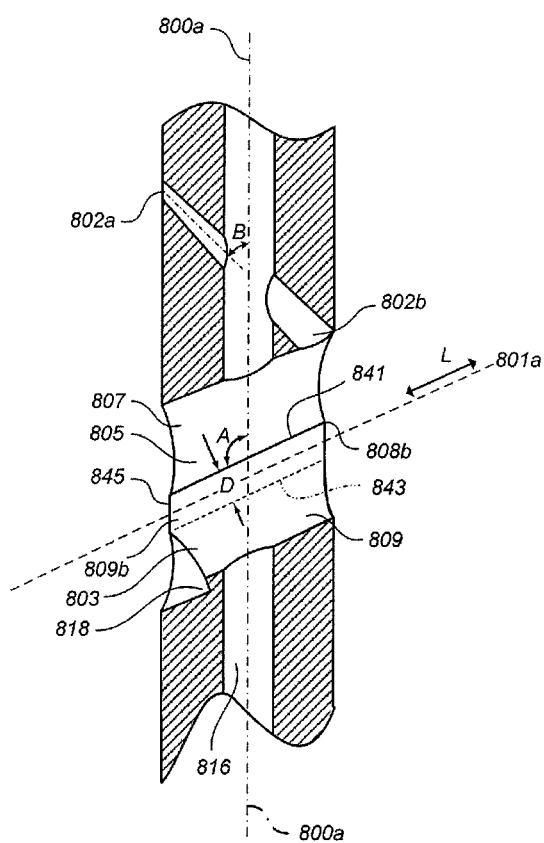
FIG. 47 is a cross-sectional view of the intramedullary nail of FIG. 45, taken along line 47-47.

The proximal section 102 has a proximal transverse aperture 118 that receives a fastening or screw assembly 200 (various versions of which are shown in FIGS. 19-41) through the intramedullary nail 100. One implementation of the proximal transverse aperture 118, shown in FIGS. 1-4, is formed from two overlapping circular apertures 120, 122, where the proximal circle aperture 120 is smaller in diameter than the distal circle aperture 122. The proximal circle aperture 120 shown has a shoulder 132 for constraining the insertion depth of the screw assembly as will be explained in more detail below. Various other apertures allowing insertion of various screw assemblies could be used as would be known to those skilled in the art. For example, FIG. 33 illustrates the intramedullary nail with a circular aperture. The implementation of FIG. 33 is described in greater detail below. FIGS. 45 through 47 illustrate another non-circular aperture, which is described in greater detail below.

The proximal section 102 illustrated in FIG. 3 has a proximal end aperture 128. The proximal end aperture 128 is threaded to allow for the insertion of a set screw that can be used to fix the rotational and translational position of a screw assembly within the proximal transverse aperture 118. A set screw may also include mechanisms for spanning a compression screw 204 (FIG. 19) and interfering with a lag screw 202 (FIG. 19) to independently restrict the rotation or translation of the lag screw 202.

As shown in FIGS. 1-6, the transition section 104 is tapered from the proximal section 102 to the distal section 106. The tapered nature of the transition section 104 creates a press fit in the intramedullary canal that controls subsidence. The tapered transition section 104 assists in preventing the nail 100 from being pressed further down into the intramedullary canal of the femur than intended.

In the implementation of the intramedullary nail 100 shown in FIGS. 1-6, the cross-section of the transition section 104 is circular, but the cross-section could vary as known to those skilled in the art. The cross-section could be anatomically derived, similar to the cross-section of the proximal section 102, oval or non-circular. In the implementation shown in FIGS. 1-6, the transition section 104 contains a distal transverse aperture 124. The distal aperture 124 allows the insertion through the intramedullary nail 100 of a distal locking screw for locking of the intramedullary nail 100.

The distal section 106 of the intramedullary nail 100 is generally cylindrical and is configured to provide a reduced bending stiffness. The implementation shown in FIGS. 1-5 has a longitudinal slot 126 through the center of the distal section 106 that forms two sides 134, 136. The slot reduces bending stiffness at the distal end of the intramedullary nail 100 and reduces the chances of periprosthetic fractures.

FIG. 1D shows an intramedullary nail 100 according to another implementation of the disclosure. This nail features, in its proximal portions, a noncircular cross section that is symmetrical with respect to its lateral-medial axis (in this case, preferably but not necessarily, oval shaped in cross-section), and which features a centered longitudinal bore (in this case, preferably but not necessarily, circular in cross-section). This nail achieves additional stability to the extent it resists twisting in the medullary canal. It also accomplishes the aim of placing more mass toward the lateral edge or aspect of the proximal cross section. Furthermore, it places additional mass toward the medial edge or aspect, and thus provides additional structure that acts as a fulcrum to decrease the mechanical advantage of the fastening assembly which when loaded is the component that imposes tensional stress on the lateral edge or aspect.

FIGS. 7-18 illustrate intramedullary nails 100 according to other implementations of the disclosure. FIGS. 7 and 13 illustrate an intramedullary nail 100 having no longitudinal bore throughout.

FIGS. 8 and 14 illustrate an intramedullary nail 100 having stiffness reduction slots 140 in the transition section 104 and the distal section 106. The stiffness reduction slots 140 reduce the bending stiffness at the distal end of the intramedullary nail 100 and could be used to receive locking screws in some implementations.

FIGS. 9 and 15 illustrate an intramedullary nail 100 having three longitudinal slots 138 in the distal section 106 and a portion of the transition section 104 forming a cloverleaf pattern. This pattern more readily permits blood flow near the intramedullary nail 100 and also reduces bending stiffness at the distal end of the nail 100.

FIGS. 10 and 16 illustrate an intramedullary nail 100 in which the distal section 106 and a portion of the transition section 104 have a series of longitudinal grooves 146. The longitudinal grooves 146 reduce bending stiffness at the distal end, provide rotational resistance, and enhance blood flow near the intramedullary nail 100.

FIGS. 11 and 17 illustrate an intramedullary nail 100 where the transition section 104 and the distal section 106 have fins 144. The fins 144 provide rotational resistance for the intramedullary nail 100.

FIGS. 12 and 18 illustrate an intramedullary nail 100 having barbs 142 located on the distal section 106 and a portion of the transition section 104. The barbs 142 provide rotational resistance for the intramedullary nail 100.

Intramedullary nails according to the present disclosure may be inserted into a patient by any suitable known technique. Generally, the intramedullary canal of the bone is prepared with an appropriate tool to create a void for insertion of the nail. Some portions of the void may be prepared to be about 1 millimeter larger than the perimeter of the nail to permit sufficient space for blood flow after insertion of the nail. A guide pin or wire is optionally inserted into the prepared medullary canal. The nail is then introduced into the desired position. If the nail is cannulated, the nail can be introduced over the guide wire. The position of the nail may be confirmed by image intensification.

Figure 19:
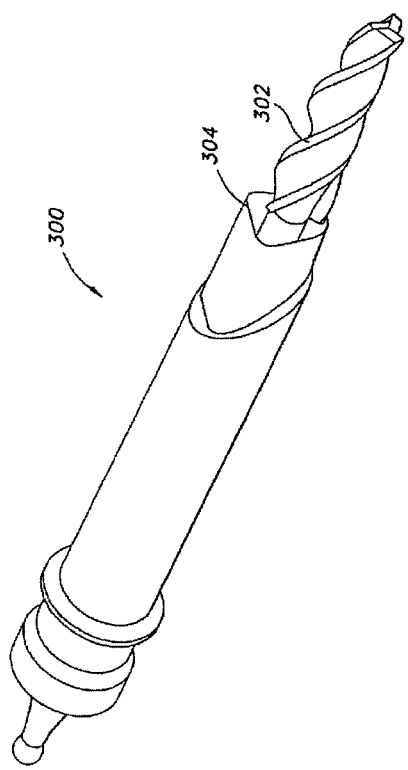
FIG. 19 is a perspective view of a tool for preparing bone to receive certain devices.

FIG. 19 shows one implementation of a tool 300 for preparing a medullary canal. The tool has a drill bit 302 for reaming and also a mortise chisel 304. In operation, the drill bit 302 reams out the medullary canal of the femur and the mortise chisel 304 cuts out a larger section in the more proximal end of a bone. As shown in FIG. 19, the mortise chisel 304 has an anatomically derived cross-section of approximately the same shape as the proximal section of the intramedullary nail. By applying this type of shaped, mortise chisel, the proximal end of the nail will be better enabled to seat on cortical bone that has been only minimally altered. The mortise chisel 304 may be of a wide variety of shapes, even complicated, asymmetrical shapes. This is advantageous because it enables a device to and method for preparing voids able to accept a wide variety of shapes of intramedullary nails without merely over-reaming circular voids. Preparation of an accurately conforming void is valuable in avoiding unnecessary removal of healthy bone, and in ensuring stable seating of the nail.

In operation, the tool 300 is advanced as a unit, with the drill bit 302 reaming and the mortise chisel 304 cutting simultaneously. The drill bit 302 may be turned with a power driver, or by hand. Likewise, the entire tool 300 may be advanced into a medullary canal manually, or advanced with the assistance of mechanical advantage or power equipment. In other configurations, the drill bit 302 may be cannulated (not shown) such that the entire tool 300 is operable over and guided by a guide wire that has been inserted into the medullary canal.

In other implementations, the bit for reaming is a more traditional reamer that is separate from a cutting tool such as the mortise chisel 304. The method for preparing a void in such an instance would include first reaming an opening with a traditional reamer. A device such as a chisel or a broach, shaped similar to the intramedullary nail to be implanted, would then be used to prepare the void. The chisel or broach may be driven in by hand, with the assistance of a hammer or mallet, or with the use of other power equipment. A nail consistent with the void prepared would then be implanted.

Other custom instruments such as a contoured broach or a custom router bit and template could be used as well. Broaches have long been used to prepare openings for hip stems, and the use of a broach would be familiar to one of skill in the art. A router bit and template could be use, in effect, to mill out the desired shape in the bone. Such a method might also be used in combination with reaming or broaching to create the desired void.

The intramedullary nails of the present disclosure can be used to treat proximal femoral fractures and femoral shaft fractures, among other fractures of long bones. When used to treat femoral shaft fractures, the intramedullary nail is secured in the femur by one or more fastening devices. When used for the treatment of proximal femoral fractures the intramedullary nail is preferably used in conjunction with a proximal fastener assembly.

Figure 20:
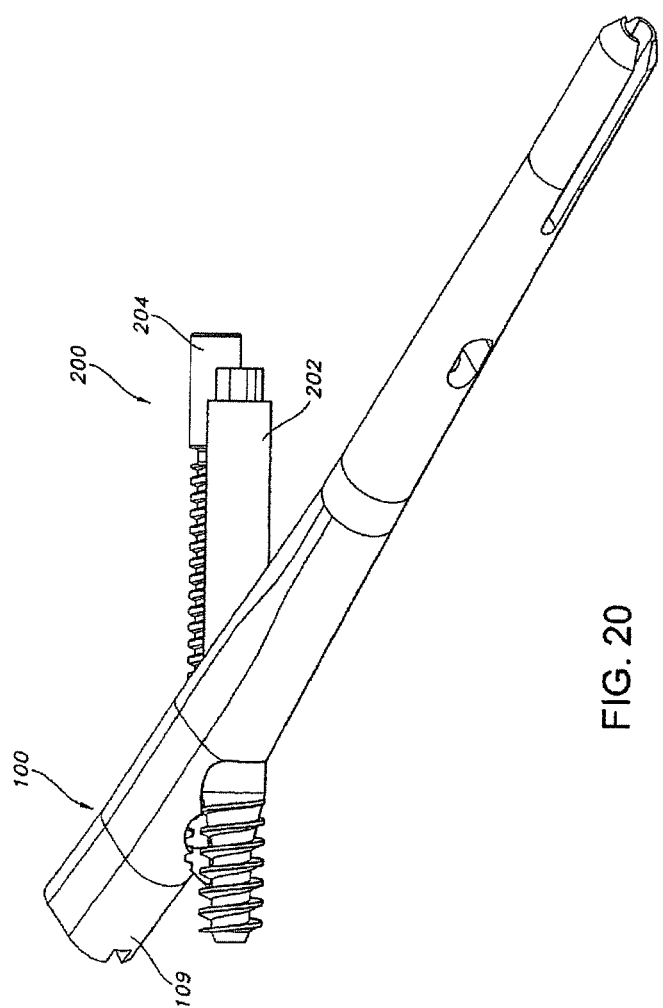
FIG. 20 is a perspective view of a device which includes a version of a fastener assembly.
Figure 29:
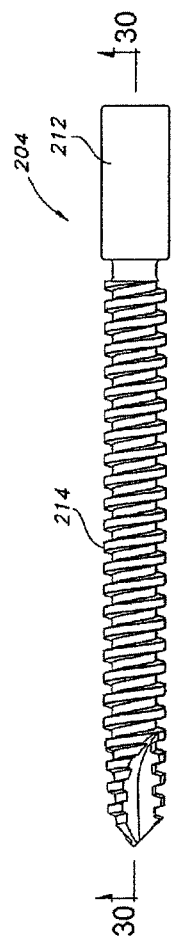
FIG. 29 is an elevation view of the compression device of the fastener assembly of FIG. 22.
Figure 30:
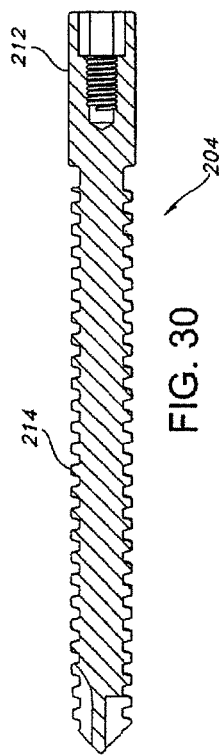
FIG. 30 is a cross-section view of the compression device of FIG. 29 shown through line 30-30.
Figure 31:
FIG. 31 is an end view of one end of the compression device of FIG. 29.
Figure 32:
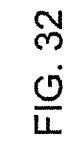
FIG. 32 is an end view of the other end of the compression device of FIG. 29.

FIGS. 20 and 21 illustrate an intramedullary nail 100 used in conjunction with a fastener assembly 200. This type of fastener assembly may be used in various other bones and to treat a number of other indications, but for the purpose of providing an example, it is described here in use with the proximal femur. In general, the fastener assembly 200 is useful in any situation where one fragment of a bone is to be drawn back toward or pushed away from another fragment of the bone in a controlled manner. The fastener assembly provides the additional advantage of being configurable to allow sliding of the assembly in a desired direction after the movement of the bone fragments has been accomplished.

As shown in FIG. 21, the axis of the proximal transverse aperture 118 in the intramedullary nail 100 is angled relative to the proximal section 102 and, in use, is directed towards the femoral head. In this implementation of the fastener assembly 200, an engaging member such as a lag screw 202 is used in conjunction with a compression device, such as a compression screw 204 or a compression peg. The screws are configured such that when in use the circumference of the lag screw 202 partially intersects with the circumference of the compression screw 204, so that the compression screw 204 nests partially within the circumference of the lag screw 202. This particular combination of lag screw 202 and compression screw 204 are further illustrated in FIGS. 22 through 32. Briefly, the lag screw 202 shown in these figures is intended to engage the femoral head and to slide in the transverse aperture 118 of the nail 100. The compression screw 204 engages a shoulder 132 or other structure of the nail 100 within the transverse aperture 118 and also threads in the portion of lag screw 202 within which compression screw 204 nests, so that rotation of compression screw 204 controls sliding of the lag screw 202 relative to the nail 100 and thus compression of the femoral head against the fracture site.

The lag screw 202 shown in these drawings includes an elongate body 206 and threaded end 208. As shown in FIGS. 24 and 25, the threaded end 208 does not include a sharp end, which reduces the possibility of the cut out through the femoral head. The elongate body 206 includes a channel 212 that allows for the positioning of the compression screw 204 partially inside the circumference of the lag screw 202. The channel 212 includes a threaded portion 210 that compliments and cooperates with a threaded section 214 of the compression screw 204. The compression screw 204 includes the threaded section 214 and a head section 215. The threaded section 214 of the compression screw 204 is configured such that the threads are relatively flat and smooth at the exterior surface so that they can easily slide in the aperture and also reduce the possibility of cut out.

The lag screw 202 is received in the proximal transverse aperture 118 and into a pre-drilled hole in the femur so that the lag screw 202 extends across the fracture and into the femoral head. The threaded end 208 of the lag screw 202 engages the femoral head as the lag screw 202 is rotated within aperture 118 causing its threaded end 208 to engage the femoral head. The threaded end 208 may be any device for obtaining purchase in the femoral head, and includes but is not limited to, threads of any desired configuration including helices, barbs, blades, hooks, expanding devices, and the like. The placement depth of the lag screw 202 into the femoral head differs depending on the desired compression of the fracture.

The compression screw 204 can also be received through the proximal transverse aperture 118 into a predrilled hole in the femoral head. The threaded section 214 of the compression screw 204 engages with the threaded portion of the channel 212 of the lag screw 202. The proximal transverse aperture 118 includes the interior shoulder 132 (FIG. 21) to limit the sliding of the compression screw 204 in the general medial direction and, therefore, to limit the sliding of the lag screw 202, through the aperture 118. When the compression screw 204 is tightened, the compression screw threads 214 engage with the lag screw channel threaded portion 210 and the compression screw 204 moves in the generally medial direction down the lag screw 202. The head section 215 of the compression screw 204 engages the shoulder 132 of the proximal transverse aperture 118 preventing the compression screw 204 from moving further in the general medial direction. As the compression screw 204 is tightened, the lag screw 202 is drawn in the general lateral direction toward the intramedullary nail providing compression to the fracture. The compression screw 204 partially intersecting the circumference of the lag screw 202 provides greater surface resistance and aids in the prevention of femoral head rotation. The compression screw 204 therefore acts not only as a part of the mechanism for moving fragments of the fractured bone relative to one another, but also directly contacts bone of the femoral head to help prevent the femoral head from rotating about the axis of the lag screw 202.

In one implementation, a set screw (not shown), positioned in the proximal end aperture 128 of the intramedullary nail, is used to engage the compression screw 204 and fix the compression screw 204 and lag screw 202 in place. The use of the set screw to fix the fastener assembly 200 in place is fracture pattern dependent. If a set screw is not used to engage the fastener assembly, the fastener assembly 200 can slide within the proximal aperture limited by the shoulder 132.

In the implementation of the lag screw and compression screw shown in FIGS. 20-32, the diameter of the compression screw 204 is smaller than the diameter of the lag screw 202. The diameters of the lag screw 202 and compression screw 204 could be the same or the diameter of the lag screw 202 could be smaller than the diameter of the compression screw 204. The threads of the lag screw 202 and the compression screw 204 could be a variety of different shapes as known to those skilled in the art. In general, the purpose of the lag screw 202 is to obtain purchase in bone, and the purpose of the compression screw 204 is to engage with and draw or move the lag screw. Any configuration that permits these functions is within the scope of the disclosure.

The fastener assembly 200 could additionally be configured to allow the addition of a prosthetic femoral head and neck. In such an implementation, the lag screw 202 would be replaced with a prosthetic head and neck. The neck would fit into the proximal transverse aperture 118 in the nail 100. The design would be beneficial where degeneration or re-injury of a repaired femoral fracture and hip joint later necessitated a total hip arthroplasty (THA). The decision to accomplish a THA could be made interoperatively, or after some period of time. Instead of having to prepare a femur to accept a hip stem as is known in association with THA, only a small portion of bone would need to be removed, along with the fastener assembly 200. The prosthetic head and neck could then be inserted into the proximal transverse aperture 118, the acetabulum prepared, and the remainder of the THA completed.

FIG. 33 is a cross-section view of an intramedullary nail 100 according to another implementation of the disclosure with an alternate fastener assembly 400. The fastener assembly 400 illustrated is very similar to the compressing fastener assembly of Smith & Nephew's IMHS® system, as is more thoroughly disclosed in U.S. Pat. No. 5,032,125, which is hereby incorporated by reference, and various related international patents. The improvement of the device illustrated is that it includes the intramedullary nail 100 with an anatomically derived shape and its multiple advantages as discussed above. In operation, a sleeve 401 fits through the intramedullary nail 100, and may be secured to the nail by set screw, or other effective mechanisms. A sliding lag screw 402 is able to move axially within the sleeve 401. A compressing screw 404 is threaded into the sliding lag screw 402 such that tightening of the compressing screw 404 draws the sliding lag screw 402 back into the sleeve 401. With this mechanism, a bone fragment may be brought into a desired position, but still permitted to achieve sliding compression once positioned.

FIGS. 34-35 illustrate a fastener assembly 200 according to another implementation of the disclosure having a lag screw 202 and a compression peg 502. As shown in FIG. 34, the lag screw 202 and the compression peg 502 are configured such that, when in use, the circumference of the lag screw 202 partially intersects with the circumference of the compression peg 502, although in some implementations the circumferences might be adjacent rather than intersecting. The lag screw 202 includes an elongate body 206 and threaded end 208. The lag screw 202 has a key 504 on the channel 212. The compression peg 502 has a slot 503 that is adapted to receive the key 504 of the lag screw 202. The key 504 and slot 503 can be a variety of complimentary shapes, such as, when considered in cross section, triangular, D-shaped, key-holed and other shapes as are apparent to those skilled in the art. In operation, the compression peg 502 may be moved relative to the lag screw 202 by a compression tool (not shown) that applies disparate forces between the compression peg 502 and the lag screw 202, or between the entire assembly and the intramedullary nail 100.

In the fastener assembly 200 shown in FIGS. 34-35, the lag screw 202 is received to slide in a proximal aperture of the intramedullary nail so that the lag screw 202 extends across the break and into the femoral head. The threaded end 208 of the lag screw 202 engages the femoral head. Once the lag screw 200 has been properly engaged with the femoral head, the compression peg 502 is inserted in the proximal aperture into a predrilled hole in the femoral head, in order to prevent further rotation of the lag screw 202 as the slot 503 of the compression peg 502 receives the key 504 of the lag screw 202. By providing more area for resistance, the compression peg 502 helps to prevent the rotation of the femoral head on the lag screw 202. The compression peg 502 is fixed in position in the intramedullary nail 100 by a set screw positioned in the proximal end aperture of the nail. The lag screw 202 can slide on the compression peg 502 through the proximal aperture. In another implementation, the compression peg 502 has barbs on its surface.

A fastener assembly 200 according to another implementation of the disclosure is illustrated in FIGS. 36-37 and has a compression peg 502 and a lag screw 202 similar to the implementation illustrated in FIGS. 34-35 except that the key 504 of the lag screw 202 and the slot 503 of the compression peg 502 have complimentary ratchet teeth 506. The compression peg 502 is fixed in position in the intramedullary nail by a set screw positioned in the proximal end aperture. Compression of the fracture can be achieved by pulling the lag screw in the general lateral direction. The ratchet teeth 506 allow the lag screw 202 to move in the general lateral direction, but prevent the lag screw 202 from moving in the general medial direction. A compression tool similar to the tool describe in association with FIGS. 34-35 may be used to accomplish the movement.

FIGS. 38-39 illustrate a fastener assembly 200 having a lag screw 602, a cross hair screw 610 and a compression screw 604. The lag screw 602 includes an elongate body 606 and threaded end 608. The elongate body 606 is semi-circular shaped in cross section. The screws 602, 604, 610 are configured so that the circumference of the lag screw 602 intersects with the circumferences of the cross hair screw 610 and the compression screw 604. The elongate body 606 of the lag screw 602 is threaded to compliment and cooperate with a threaded section of the cross hair screw 610. The cross hair screw 610 is threaded to engage with the lag screw 602 and the compression screw 604. The compression screw 604 includes a threaded portion 614 and a head portion 612.

In the implementation of FIGS. 38-39, the lag screw 602, the cross hair screw 610 and the compression screw 604 are received simultaneously to slide in a proximal aperture of an intramedullary screw. The lag screw 602 extends across the break and into the femoral head. The threaded end 608 of the lag screw 602 engages the femoral head. As compression screw 604 is tightened, the threads 614 of the compression screw engage the threads of the cross hair screw 610 and lag screw 602, thereby moving the lag screw 602 in the general lateral direction toward the intramedullary nail providing compression to the femoral head. The cross hair screw 610 is then turned causing the compression screw 604 to move in the distal direction away from the lag screw 602. The fastener assembly 200 can alternatively be configured so that the compression screw 604 moves proximally relative to the lag screw 602. The compression screw 604 separate from the lag screw 602 helps to prevent rotation of the femoral head on the lag screw 602 by adding more area for resistance.

FIGS. 40-41 illustrate a fastener assembly 200 having a lag screw 702 and a compression peg 704. The lag screw 702 includes an elongate body 706 and a threaded end 708. The elongate body 706 is semi-circular shaped in order to allow the compression peg 704 to be positioned partially inside the circumference of the lag screw 702 for insertion into the femur and has a key 712 positioned on the interior side of the elongate body 706. The elongate body 706 also has an aperture 710 through the body. The compression peg 704 is generally cylindrical and is sized to fit within the semi-circular body 706 of the lag screw. The key 712 of the lag screw is received by a slot 714 in the compression peg 704. The key 712 and slot 714 contain complimentary ratchet teeth.

The lag screw 702 and the compression peg 704 are received simultaneously to slide in a proximal aperture of an intramedullary screw into a pre-drilled hole in the femur. The lag screw 702 extends across the break and into the femoral head. The threaded end of the lag screw 702 engages the femoral head. A compression tool similar to the tool described in association with FIGS. 34-35 may be used to accomplish movement between the compression peg 704 and the lag screw 702, or between the entire assembly and the intramedullary nail 100. A set screw may used to fix the position of the fastener assembly. The set screw is configured such that when the set screw is tightened a protrusion on the set screw is received through the slot 710 of the lag screw 702 and moves the compression screw 704 away from the lag screw 702. The compression screw 704 separate from the lag screw 702 helps to prevent rotation of the femoral head on the lag screw by adding more area for resistance.

Figure 42:
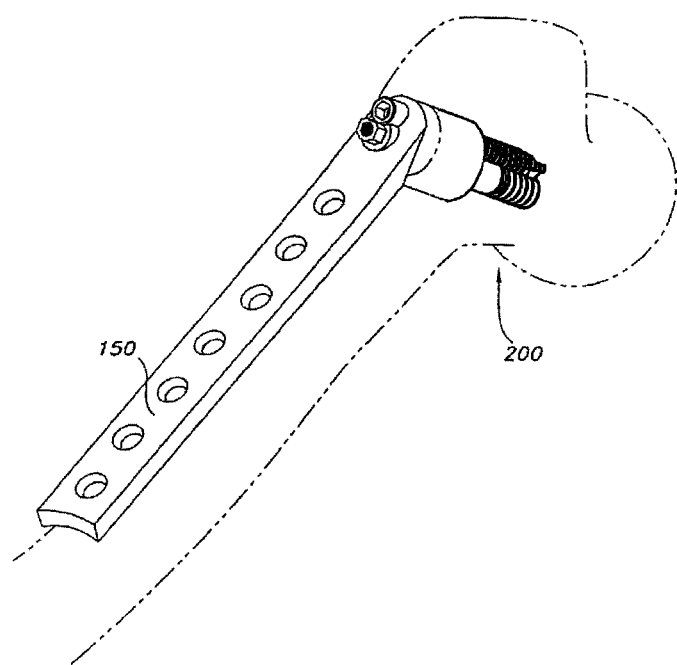
FIG. 42 is a perspective view of a compression plate which includes a fastener assembly.
Figure 43:
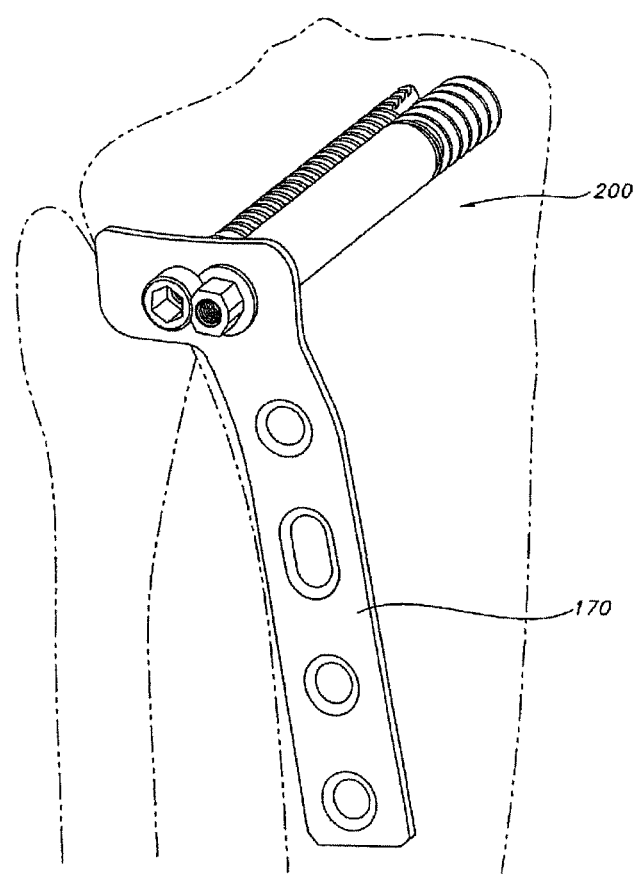
FIG. 43 is a perspective view of a periarticular plate which includes a fastener assembly.

FIG. 42 illustrates another implementation where a fastener assembly 200 is employed in cooperation with a compression plate 150. As illustrated, the devices are being applied to a femur. The various implementations of the fastener assembly 200 disclosed above may be used with a similar compression plate, and various compression plates may be configured to be applicable to other parts of the anatomy. For example, FIG. 43 illustrates another implementation where a fastener assembly 200 is being used with a periarticular plate 170. The plate and fastener assembly shown are being applied to a proximal tibia.

Figure 44:
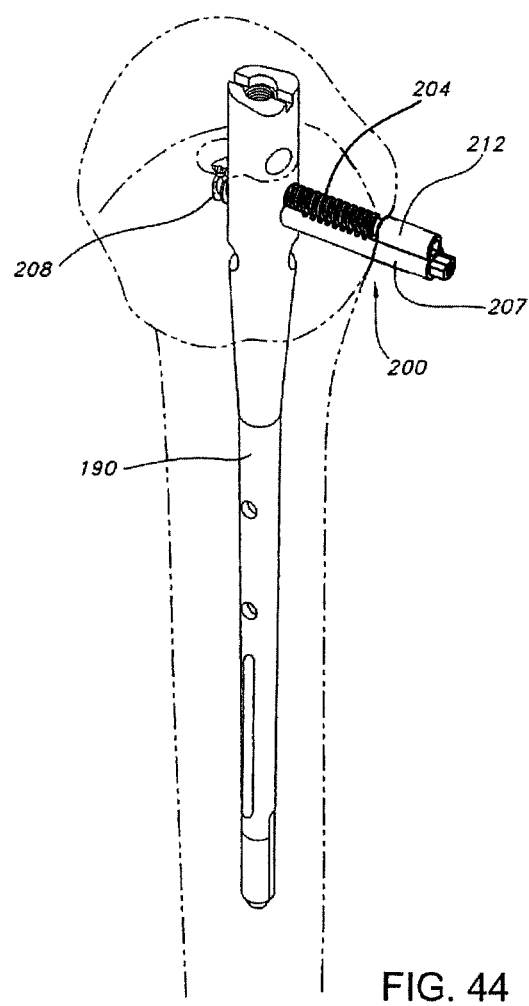
FIG. 44 is a perspective view of a device used in the context of humeral repair in a shoulder joint.

FIG. 44 illustrates another implementation where a fastener assembly 200 is used in combination with a humeral nail 190. As illustrated, a head section 212 of compression screw 204 bears against the humerus to draw compression against the humerus. With the compression force applied to lag screw 202, and the lag screw 202 affixed to a bone fragment through its threaded end 208, the bone fragment may be drawn into position for proper healing. In some circumstances, it may be advantageous to place a washer or bearing surface (not shown) between the head section 212 and the humeral bone against which the head section 212 compresses. In yet another variant, the opening in the humerus may be enlarged such that head section 212 is permitted to penetrate the humerus and bear against a portion of the humeral nail 190. In such an implementation, the fastener assembly 200 would be shorter than illustrated in FIG. 45 to obtain purchase in the same area of bone with the threaded end 208.

Referring to FIGS. 45-47, a universal femoral nail 800 defines a reconstruction aperture 801 for treating fractures or other injury to the femoral head and neck in a reconstruction mode and targets the femoral head and neck, as described above, and an antegrade aperture 802 for treating fractures of the femoral shaft in an antegrade mode and targets the lesser trochanter. The nail 800 includes a central long axis 800a, a head 800b formed at a proximal portion 812 of the nail 800 and a shaft 813 extending from the head 800b to a distal portion 814 of the nail 800. The cross-sectional shape of the head 800b in a plane perpendicular to the long axis 800a is generally non-circular. As illustrated in FIG. 50, the cross-sectional shape of the head 800b is generally trapezoidal and includes rounded portions. For example, at least a portion of a lateral side 800d is flat. However, the medial side 800e is generally rounded. As also illustrated in FIG. 50, a medial to lateral plane M-L bisects the head 800b, includes a central through axis 801a of the reconstruction aperture, and includes the central long axis 800a of the nail 800. Thus, as illustrated, the medial to lateral plane M-L is coplanar with a coronal plane of the nail 800 that separates the front of the nail from the back of the nail. It should be noted that this plane is not necessarily related to a coronal plane of a patient's body or even a coronal plane of a patient's femur. Additionally, in some implementations, the reconstruction aperture 801 is not centrally disposed in the head 800b such that the medial to lateral plane M-L does not include the central through axis 801a, but the medial to lateral plane M-L is then parallel to a central through axis 801a of the reconstruction aperture 801, and parallel to the coronal plane of the nail 800.

The reconstruction transverse aperture 801 is "light bulb" shaped and oriented off the long axis 800a of the nail 800, and is configured to receive a lag member and a compression member, such as the lag screw 202 and the compression screw 204 described above. To target the femoral head and neck in the reconstruction mode, the central through axis 801a of the reconstruction aperture 801 lies in the medial to lateral plane M-L, and is oriented at an angle A of about 122 degrees relative to the central long axis 800a. The antegrade transverse aperture 802 is also oriented off the long axis 800a by an angle B, which is about 35 degrees. The antegrade aperture 802 is oriented such that a central through axis 802a of the antegrade aperture 802 lies in an antegrade plane AP, which is parallel to the long axis 800a and is radially offset from the medial to lateral plane M-L by an angle C of approximately 12 degrees. As illustrated in FIG. 50, the antegrade aperture 802 is not centered in the head 800b, such that the central through axis 802a of the antegrade aperture 802 does not intersect the long axis 800a of the nail 800. In some implementations, and as illustrated in FIG. 50, the central through axis 802a intersects the medial to lateral plane M-L proximate the medial side 800e.

As shown in FIGS. 48 and 49, the nail 800 also includes three holes 831, 832, and 833 located in a distal section 814 of the nail that, in use, can receive pins or screws to stabilize the distal section of the nail 800. The most proximal hole 831 is formed as a slot, and the central and most distal holes 832 and 833 are formed as circular holes. When treating fractures of the femoral shaft, as discussed above, bone pins or other fasteners (not shown) are disposed within one or more of the three holes 831, 832, and 833 and secured to healthy bone.

The most proximal hole 831 and the most distal hole 833 are formed such that respective central through axes 831a and 833a of the most proximal hole 831 and the most distal hole 833 lie in planes that are parallel to the antegrade plane AP. In other words, the central through axes 831a and 833a are radially offset from the medial to lateral plane M-L by the same angle as the central through axis 802c of the antegrade aperture 802. Thus, the antegrade aperture 802, the most proximal hole 831 and the most distal hole 833 can be said to be parallel, or lie in parallel planes, even though they may be oriented differently with respect to the central axis 800a of the nail 800. For example, as discussed above, the central through axis 802a of the antegrade aperture 802 is oriented at 35 degrees with respect to the central long axis 800a of the nail 800. However, the most proximal hole 831 and the most distal hole 833 may be formed at approximately 90 degrees to the central long axis 800a, or at other angular orientations. In some implementations, the central though axis 831a of the most proximal hole 831 lies in the same plane as the central through axis 833a of the most distal hole 833. Additionally, the central through axes 831a and 833a of the most proximal hole 831 and the most distal hole 833 can lie in the antegrade plane AP such that the central through axes 802a, 831a, and 833a are coplanar.

A central through axis 832a of the central hole 832 is also radially offset from the medial to lateral plane M-L. However, the central through axis 832a is offset from the medial to lateral plane M-L by a different amount than the central through axes 831a and 833a. For example, the central through axis 832a of the central hole 832 is offset from the medial to lateral plane M-L by 37 degrees, and is radially offset from the antegrade plane AP by 25 degrees.

When treating fractures of the neck, head, and intertrochanteric regions of the femur, the nail 800 is used in conjunction with first and second members, such as the lag screw 202 and the compression screw 204, received in the reconstruction aperture 801. When treating only a fracture in the femoral shaft, the nail 800 is used in conjunction with a bone pin received in the antegrade aperture 802. Running along the long axis 800a of the nail 800 is a bore 816. A set screw (not shown) can be disposed in the bore 816 for locking the first and second members or the bone pin.

The reconstruction aperture 801 has a first semi-cylindrical aperture 810 associated with a first portion 811 (FIG. 46) of the reconstruction aperture 801, and a second U-shaped aperture 820 associated with a second portion 821 (FIG. 46) of the reconstruction aperture 801. The nail 800 includes an inner wall 805 (FIG. 47) that defines the reconstruction aperture 801. The inner wall 805 includes a first, semi-cylindrical section 807 that defines the semi-cylindrical aperture 810 and a second, U-shaped section 809 that defines the U-shaped aperture 820. As shown, except for a shoulder 803, the reconstruction aperture 801 has a constant cross-sectional shape along a length dimension, L, of the reconstruction aperture 801. Shoulder 803 is defined by an outward step 818 in the U-shaped section 809.

The semi-cylindrical section 807 of the inner wall 805 comprises an arc segment that extends more than 180 degrees, for example, 270 degrees, and terminates in two opposing edges 808a and 808b. The plane between the opposing edges 808a and 808b defines a face 841 of the semi-cylindrical section 807. The opposing edges 808a and is 808b are located at a transition, T, between the semi-cylindrical section 807 and the U-shaped section 809 of the inner wall 805. Thus, the semi-cylindrical section 807 and the U-shaped section 809 define a continuous surface of the reconstruction aperture 801.

The U-shaped section 809 of the inner wall 805 includes a semi-cylindrical arc segment 809a opposite the face 841 of the semi-cylindrical section 807 and two mutually-opposing walls 809b and 809c extending from the semi-cylindrical arc segment 809a. The U-shaped section 809 of the inner wall 805 also includes a face 845 defined by the plane between edges 809e and 809f of the walls 809b and 809c. As illustrated, the face 845 of the U-shaped section 809 is coplanar with the face 841 of the semi-cylindrical section 807. The semi-cylindrical arc segment 809a includes a face 843 that opposes the face 841 of the semi-cylindrical section 807 of the inner wall 805 (and the face 845 of the U-shaped section 809 of the inner wall 805), and is spaced therefrom by the opposing walls 809b and 809c.

In some implementations, the face 843 of the semi-cylindrical arc segment 809a is spaced from the first open face 841 of the first semi-cylindrical aperture 810 by a distance D such that a cylindrical member having a circular cross section of substantially the same diameter as the diameter of the semi-cylindrical arc segment 809a extends into the first portion 811 of the reconstruction aperture 801 when disposed in and abutting the semi-cylindrical arc segment 809a. For example, where the semi-cylindrical arc segment 809a is a 180 degree arc segment, the parallel walls 809b and 809c extend from the semi-cylindrical arc segment 809a (that is to say, from the face 843 of the semi-cylindrical arc segment 809a) the distance, D, which is less than the radius of the semi-cylindrical arc segment 809a. In some implementations, the diameter of the semi-cylindrical arc segment 809a is between about 5 millimeters and about 15 millimeters, and the amount of overlap of such a cylindrical member with a cylindrical member received within the semi-cylindrical section 807 is between about 1 millimeter and 5 millimeters.

As illustrated, the opposing walls 809b and 809c are parallel and the semi-cylindrical arc segment 809a is a 180 degree arc segment. Alternatively, however, the opposing walls 809b and 809c can be divergent, and/or the semi-cylindrical arc segment 809a can be an arc segment less than 180 degrees. Thus, when a member that is sized to fit within the semi-cylindrical arc segment 809a is disposed in the U-shaped aperture 820, the member is not constrained by a narrowing of the U-shaped aperture 820. As such, a member that is sized to fit within the semi-cylindrical arc segment 809a is constrained from moving into the semi-cylindrical aperture 810 only when a second member is disposed in the semi-cylindrical aperture 810. For example, when a compression screw 204 is disposed within the U-shaped section 809 of the inner wall 805 and a lag screw 202 is disposed within the semi-cylindrical section 807 of the inner wall 805, the compression screw 204 is constrained to remain in the U-shaped section 809, and the lag screw 202 and the compression screw 204 cooperate to resist a force moment applied to one or both of the lag screw 202 and the compression screw 204. However, if the lag screw 202 is not present within the semi-cylindrical section 807 of the inner wall 805, then the compression screw 204 can move in response to forces applied to the compression screw 204, such that occurrence of bending or breaking of the compression screw 204 is reduced.

Referring additionally to FIGS. 48-52, the antegrade aperture 802 includes a first opening (or entry) 802a formed in a lateral side 800d of the nail 800 that is proximal to a first opening (or entry) 801a of the reconstruction aperture 801 formed in the lateral side 800d of the nail 800. The first opening 801a of the reconstruction aperture 801 is generally centered on the lateral side 800d of the nail 800 and the first opening 802a of the antegrade aperture 802 is not centered on the lateral side 800d of the nail 800. The non-circular cross-sectional shape of the head 800b with a larger lateral side 800d than medial side 800e provides additional surface area for locating the first opening 802a of the antegrade aperture 802 off-center within the head 800b, and can provide increased strength compared to a head having a circular cross-sectional shape when the antegrade aperture 802 is oriented off the medial to lateral plane M-L.

Additionally, while the reconstruction aperture 801 is oriented in the direction of a femoral neck such that the second opening (or exit) 801b of the reconstruction aperture 801 formed in a medial side 800e of the nail 800 is proximal to the first opening 801a of the reconstruction aperture 801, the antegrade aperture 802 is oriented distally towards a second opening (or exit) 802b that is formed in the inner wall 805 at a location proximate to the second opening 801b of the reconstruction aperture 801 formed in the medial side 800e of the nail 800. However, in some implementations, the second opening 802b of the antegrade aperture 802 can be formed in the medial side 800e of the nail 800, and the second opening 802b can be located proximally or distally of the second opening 801b of the reconstruction aperture 801.

As shown in FIGS. 51 and 52, the exit opening 802b is formed on the medial side 800e of the nail 800 such that the exit opening 802b is contained entirely within the exit opening 801b of the reconstruction aperture 801. For given dimensions of the antegrade aperture 802 and the reconstruction aperture 801, the co-location of the exit openings 802b and 801b reduces an amount of material that is removed from the medial side 800e of the nail 800. As mentioned above, the non-circular cross-sectional shape of the head 800b allows for the co-location of the exit openings 802b and 801b in conjunction with the radial offset of the antegrade plane AP and the medial to lateral plane M-L while maintaining structural strength of the head 800b.

In some implementations, as illustrated in FIGS. 58 and 59, the head 800b of the nail 800 is angled from the shaft 813 by an angle D, such as a 5 degree angle. The bend is formed in the antegrade plane AP such that a tangent of the long axis 800a at a location 831 in the head 800b makes an angle of approximately 5 degrees relative to a tangent of the long axis 800a at a location 833 in the shaft 813. As illustrated, the head 800b and the shaft 813 are both generally straight in the antegrade plane AP. As illustrated in FIGS. 59 and 60, the nail 800 is curved perpendicular to the antegrade plane AP such that the antegrade plane AP is also curved. The curve illustrated in FIG. 60 is compound, having more than one radius of curvature perpendicular to the antegrade plane AP.

As those skilled in the art will appreciate, the particular implementations described above and illustrated in the figures are provided for illustration, and various alterations may be made in the structure and materials of the illustrated implementations. For example, while the non-circular aperture of FIGS. 45-47 is illustrated with circular semi-cylindrical portions, the non-circular aperture can have semi-cylindrical portions having other cross-sectional shapes, such as oval or rectangular. Accordingly, fastening members with corresponding shapes, i.e., cylindrical fasteners having square, rectangular, oval, crescent, or other cross-sectional shapes can be used. Furthermore, the non-circular aperture may have additional portions, which may or may not be cylindrical. Additionally, one or more of the apertures 831, 832, 833 located near the distal end 800c can be angled other than perpendicularly to the axis 800a having a first opening located proximally or distally of a second opening thereof. Furthermore, in general, the cross-sectional shape of the shaft 813 in a plane perpendicular to the long axis 800a is substantially circular, although the diameter of the shaft 813 can be varied along the long axis 800a. For example, all or a portion of the shaft 813 can be tapered. Also, the head 800b can be formed in other cross-sectional shapes, including circular, oval, or polygonal, for example. However, where other shapes are selected for the head 800b, the medial to lateral plane M-L still includes the central long axis 800*a* and is parallel to or includes the central through axis 801*a* of the reconstruction aperture 801. Additionally, the transverse aperture 801 can be oriented such that the angle A can be from about 110 degrees to about 150 degrees, or from about 120 degrees to about 130 degrees. The central through axis 832*a* of the central hole 832 can be offset from the medial to lateral plane M-L and the antegrade plane AP by other amounts, such as by an angle from about 20 to about 75 degrees, or from about 30 degrees to about 60 degrees. The angle C can be from about 0 degrees to about 30 degrees, from about 0 degrees to about 20 degrees, or from about 10 degrees to about 15 degrees. The angle D can be from about 0 to about 20 degrees, or from about 0 to about 10 degrees. The central through axis 832*a* of the central hole 832 can be radially offset from the antegrade plane by an angle from about 0 to about 90 degrees, or from about 0 to about 45 degrees.

What is claimed is:

1. A femoral intramedullary nail, comprising:
   a shaft having a proximal region, a distal region, a medial side, a lateral side, and a central longitudinal axis extending proximally and distally, the proximal region having a non-circular cross-sectional shape perpendicular to the longitudinal axis;
   a reconstruction aperture in the proximal region for receiving at least one member in a reconstruction mode, the aperture oriented to target a femoral head and neck; and
   an antegrade aperture in the proximal region for receiving at least one member in an antegrade mode, the antegrade aperture oriented to target a lesser trochanter, the antegrade aperture having a central through axis, wherein the antegrade aperture includes an exit opening located within the reconstruction aperture;
   wherein the reconstruction aperture extends from the medial side to the lateral side of the nail and the central through axis of the antegrade aperture is offset from the central longitudinal axis of the nail such that the central through axis of the antegrade aperture does not intersect the central longitudinal axis of the nail.

2. The intramedullary nail of claim 1, wherein the reconstruction aperture comprises two overlapping apertures.

3. The intramedullary nail of claim 1, wherein the shaft comprises a head portion in the proximal region, the head portion having a cross-sectional shape perpendicular to the longitudinal axis that is different from a cross-sectional shape perpendicular to the longitudinal axis of the distal region of the shaft.

4. The intramedullary nail of claim 3, wherein the longitudinal axis within the head portion is angled from the longitudinal axis in the distal region.

5. The femoral intramedullary nail of claim 1, wherein the reconstruction aperture is defined by:
   parallel inner walls of the shaft;
   a first semi-cylindrical section having an arc greater than 180 degrees; and
   a second semi-cylindrical section located opposite the first semi-cylindrical section.

6. The femoral intramedullary nail of claim 5, wherein the second semi-cylindrical section has a radius, and wherein the parallel walls have a height along the central longitudinal axis, the height being less than the radius of the second semi-cylindrical section.

7. The femoral intramedullary nail of claim 5, wherein the first semi-cylindrical section defines a first portion of the reconstruction aperture, wherein the parallel inner walls and the second semi-cylindrical section define a second portion of the reconstruction aperture, and wherein the second portion of the reconstruction aperture is sized such that a cylindrical member of substantially the same diameter as the second semi-cylindrical section can pass out from the second portion of the reconstruction aperture toward the first portion of the reconstruction aperture.

8. A femoral intramedullary nail, comprising:
   a shaft having a proximal region, a distal region, a medial side, a lateral side, and a longitudinal axis extending proximally and distally;
   a reconstruction aperture in the proximal region for receiving at least one member in a reconstruction mode, the reconstruction aperture oriented to target the femoral head and neck;
   an antegrade aperture in the proximal region for receiving at least one member in an antegrade mode, the antegrade aperture oriented to target the lesser trochanter; and
   a distal aperture in the distal region, the reconstruction aperture, the antegrade aperture, and the distal aperture each having a central through axis;
   wherein the central through axis of the antegrade aperture lies within an antegrade plane, the antegrade plane being parallel to the longitudinal axis, wherein the central through axis of the distal aperture lies in one of the antegrade plane and a plane parallel to the antegrade plane, and wherein the central through axis of the reconstruction aperture intersects the antegrade plane and extends out of the antegrade plane.

9. The intramedullary nail of claim 8, wherein the antegrade aperture includes an exit opening located within the reconstruction aperture.

10. The intramedullary nail of claim 8, wherein the reconstruction aperture comprises two overlapping apertures.

11. The intramedullary nail of claim 8, wherein the reconstruction aperture comprises two discrete apertures.

12. The intramedullary nail of claim 8, wherein the shaft comprises a head portion in the proximal region, the head portion having a non-circular cross section perpendicular to the longitudinal axis.

13. The intramedullary nail of claim 12, wherein the longitudinal axis within the head portion is angled from the longitudinal axis in the distal region.

14. An intramedullary nail, comprising:
   a shaft having a proximal region, a distal region, a medial side, a lateral side, and a longitudinal axis extending proximally and distally, the shaft including an inner wall having opposing planar portions;
   a reconstruction aperture in the proximal region for receiving at least one member in reconstruction mode, the reconstruction aperture having an entry opening substantially on the lateral side of the shaft and an exit opening substantially on the medial side of the shaft, wherein the reconstruction aperture is partially defined by the opposing planar portions of the inner wall; and
   an antegrade aperture in the proximal region for receiving at least one member in an antegrade mode, the antegrade aperture having an entry opening substantially on the lateral side of the shaft and an exit opening substantially on the medial side of the shaft, wherein the antegrade aperture exit opening is located within the reconstruction aperture exit opening.

15. The intramedullary nail of claim 14, wherein the reconstruction aperture comprises two overlapping apertures.

16. The intramedullary nail of claim 14, wherein the reconstruction aperture comprises two discrete apertures.

17. The intramedullary nail of claim 14, wherein the shaft comprises a head portion in the proximal region, the head portion having a non-circular cross section perpendicular to the longitudinal axis.

18. The intramedullary nail of claim 17, wherein the longitudinal axis within the head portion is angled from the longitudinal axis in the distal region.

19. The intramedullary nail of claim 14, wherein a central through axis of the antegrade aperture intersects a plane that includes a central through axis of the reconstruction aperture.

20. An intramedullary nail comprising:
a first transverse aperture that is non-circular and has a central through axis, the first transverse aperture including a shoulder and being configured to receive a compression assembly, and the first transverse aperture including an entry on a lateral side of the nail and an exit on a medial side of the nail; and
a second transverse aperture having a central through axis, the second transverse aperture having an entry on the lateral side of the nail and an exit on the medial side of the nail within the exit of the first transverse aperture,
wherein the central through axis of the first transverse aperture is included in a plane that includes or is parallel to a central long axis of the nail, and
wherein the central through axis of the second transverse aperture is oriented at an angular offset with respect to the plane.

21. The intramedullary nail of claim 20, further comprising a head, the first transverse aperture and the second transverse aperture being located in the head, and further comprising a third transverse aperture located proximate a distal end of the nail.

22. The intramedullary nail of claim 21, wherein the head is angled relative to the long axis.

23. The intramedullary nail of claim 20, further comprising a bore extending in a direction of the long axis, the bore intersecting the first transverse aperture.

24. The intramedullary nail of claim 20, wherein the first transverse aperture has a section having an arc greater than 180 degrees located opposite a U-shaped section having an arc of approximately 180 degrees.

25. The intramedullary nail of claim 20, wherein the central axis of the second transverse aperture is spaced apart from the central long axis of the nail.

26. An orthopaedic implant comprising:
a nail having a long axis, an inner wall defining a through hole oriented to target a femoral head and neck, and a first transverse aperture proximal of the through hole, the inner wall comprising:
a first semi-cylindrical section having an arc greater than 180 degrees and defining a first portion of the through hole; and
a second U-shaped section having a pair of parallel walls and a semi-cylindrical segment having an arc of approximately 180 degrees, the second U-shape section defining a second portion of the through hole;
the arc of the first semi-cylindrical section defining a first open face of the first portion of the through hole, and the parallel walls of the second U-shape portion defining a second open face of the second portion of the through hole opposing the first open face, such that a cylindrical member of substantially the same diameter as that of the second semi-cylindrical section can pass out from the second portion of the through hole toward the first portion of the through hole,
wherein the nail defines an exit opening for the through hole, and the first transverse aperture has an exit opening located within the exit opening for the through hole.

27. The orthopaedic implant of claim 26, wherein the first transverse aperture has an exit located in the inner wall.

28. The orthopaedic implant of claim 26, wherein the first transverse aperture extends along an axis that is radially-offset from the orientation of the through hole.

29. The orthopaedic implant of claim 26, wherein the nail further comprises a second transverse aperture located proximate a distal end of the nail.

30. The orthopaedic implant of claim 29, wherein the second transverse aperture extends along an axis that is non-perpendicular to the long axis of the nail.

31. The orthopaedic implant of claim 26, wherein the first transverse aperture is oriented off the long axis and has an entry located in a head of the nail, the head of the nail being angled relative to the long axis of the nail.

32. The orthopaedic implant of claim 31, further comprising a second transverse aperture located proximate a distal end of the nail, the second transverse aperture having an opening aligned with the entry of the first transverse aperture.

33. The orthopaedic implant of claim 26, wherein the first open face is spaced from the second semi-cylindrical section a distance less than the diameter of the second semi-cylindrical section, such that a cylindrical member of substantially the same diameter as that of the second semi-cylindrical section extends into the first portion of the through hole when disposed adjacent the second semi-cylindrical section.

34. A femoral intramedullary nail, comprising:
a shaft having a proximal region, a distal region, a medial side, a lateral side, and a central longitudinal axis extending proximally and distally, the proximal region having a non-circular cross-sectional shape perpendicular to the longitudinal axis;
a reconstruction aperture in the proximal region for receiving at least one member in a reconstruction mode, the aperture oriented to target a femoral head and neck, wherein the reconstruction aperture is defined by:
parallel inner walls of the shaft;
a first semi-cylindrical section having an arc greater than 180 degrees; and
a second semi-cylindrical section located opposite the first semi-cylindrical section; and
an antegrade aperture in the proximal region for receiving at least one member in an antegrade mode, the antegrade aperture oriented to target a lesser trochanter, the antegrade aperture having a central through axis;
wherein the reconstruction aperture extends from the medial side to the lateral side of the nail and the central through axis of the antegrade aperture is offset from the central longitudinal axis of the nail such that the central through axis of the antegrade aperture does not intersect the central longitudinal axis of the nail.

* * * * *